(12) United States Patent
Kampe et al.

(10) Patent No.: US 7,030,991 B1
(45) Date of Patent: Apr. 18, 2006

(54) FIELD CONDENSING IMAGING SYSTEM FOR REMOTE SENSING OF ATMOSPHERIC TRACE GASES

(75) Inventors: Thomas Ulrich Kampe, Boulder, CO (US); Brian R. Johnson, Superior, CO (US)

(73) Assignee: Ball Aerospace & Technologies Corp., Boulder, CO (US)

( * ) Notice: Subject to any disclaimer, the term of this patent is extended or adjusted under 35 U.S.C. 154(b) by 258 days.

(21) Appl. No.: 10/633,468

(22) Filed: Aug. 1, 2003

(51) Int. Cl.
*G01B 9/02* (2006.01)
*G01J 3/45* (2006.01)
*G02B 23/00* (2006.01)
*G02B 13/08* (2006.01)

(52) U.S. Cl. .................. 356/454; 356/399; 356/668
(58) Field of Classification Search ................ 356/454, 356/519; 359/399–401, 668–671
See application file for complete search history.

(56) References Cited

U.S. PATENT DOCUMENTS

| | | | |
|---|---|---|---|
| 3,432,239 A | 3/1969 | Holland ...................... 356/112 |
| 3,501,641 A | 3/1970 | Krause ........................ 250/209 |
| 3,802,777 A | 4/1974 | Regnier et al. ............... 356/75 |
| 3,824,018 A | 7/1974 | Crane, Jr. .................... 356/112 |
| 3,939,348 A | 2/1976 | Barrett ....................... 250/339 |
| 3,998,552 A | 12/1976 | Stewart et al. .............. 356/103 |
| 4,035,643 A | 7/1977 | Barrett ....................... 250/339 |
| 4,057,319 A | 11/1977 | Ash et al. .................. 350/96 C |
| 4,195,931 A | 4/1980 | Hara ........................... 356/346 |
| 4,377,324 A | 3/1983 | Durand et al. .............. 350/166 |
| 4,400,058 A | 8/1983 | Durand et al. .............. 350/166 |
| 4,509,857 A | 4/1985 | Vermande ................... 356/346 |
| 4,553,816 A | 11/1985 | Durand et al. .............. 350/166 |
| 4,583,855 A | 4/1986 | Bareket ....................... 356/351 |
| 4,615,033 A | 9/1986 | Nakano et al. | |
| 4,729,658 A | 3/1988 | Poultney ...................... 356/328 |
| 4,743,114 A | 5/1988 | Crane, Jr. .................... 356/346 |
| 4,930,131 A | 5/1990 | Sizer, II ....................... 372/18 |
| 4,937,447 A | 6/1990 | Barrett ........................ 250/339 |
| 4,962,319 A | 10/1990 | Leonard et al. ............. 250/574 |
| 4,973,853 A | 11/1990 | Leonard et al. ............. 250/574 |
| 5,088,815 A | 2/1992 | Garnier et al. ............. 356/28.5 |
| 5,144,498 A | 9/1992 | Vincent ....................... 359/885 |
| 5,159,406 A | 10/1992 | Adler et al. ................. 356/349 |
| 5,208,654 A | 5/1993 | Shao et al. .................. 356/358 |
| 5,212,585 A | 5/1993 | Ning ........................... 359/276 |
| 5,214,484 A | 5/1993 | de Mollerat du Jeu .... 356/28.5 |

(Continued)

OTHER PUBLICATIONS

William S. Heapes et al., "Fabry-Perot Interferometer for Column $Co_2$," NASA Goddard Space Flight Center, 6 pages (Jun. 2002).

(Continued)

*Primary Examiner*—Gregory J. Toatley, Jr.
*Assistant Examiner*—Partick Connolly
(74) *Attorney, Agent, or Firm*—Sheridan Ross P.C.

(57) ABSTRACT

A sensor system featuring a field angle compression telescope optical system for measuring atmospheric trace gases is provided. According to an embodiment of the present invention, the telescope optical system condenses the field angle of received light with respect to a cross track plane, while leaving the field angle with respect to an along-track plane uncompressed. Such an anamorphic telescope design provides a wide field of view, while allowing information regarding the altitude or height distribution of a gas to be obtained. According to another embodiment of the present invention, the field angle of received light is compressed by magnifying the received light by a value less than 1.0 in all directions.

33 Claims, 18 Drawing Sheets

U.S. PATENT DOCUMENTS

| | | | | |
|---|---|---|---|---|
| 5,218,426 | A | 6/1993 | Hall et al. | 356/361 |
| 5,339,155 | A | 8/1994 | Partridge et al. | 356/419 |
| 5,539,517 | A | 7/1996 | Cabib et al. | 356/346 |
| 5,539,518 | A | 7/1996 | Bennett | 356/346 |
| RE35,355 | E | 10/1996 | Ryan et al. | 250/343 |
| 5,606,419 | A | 2/1997 | Foosnaes et al. | 356/419 |
| 5,666,225 | A * | 9/1997 | Colboume | 359/589 |
| 5,719,989 | A | 2/1998 | Cushing | 359/589 |
| 5,731,889 | A | 3/1998 | Jeong et al. | 359/258 |
| 5,801,831 | A * | 9/1998 | Sargoytchev | 356/454 |
| 5,835,214 | A | 11/1998 | Cabib et al. | 356/346 |
| 5,999,322 | A | 12/1999 | Cushing | 359/589 |
| 6,046,854 | A | 4/2000 | Bhagavatula | 359/577 |
| 6,075,597 | A | 6/2000 | Olshausen | 356/345 |
| 6,118,421 | A | 9/2000 | Kawaguchi et al. | 345/89 |
| 6,163,380 | A | 12/2000 | Hays | 356/519 |
| 6,243,170 | B1 * | 6/2001 | Ershov | 356/519 |
| 6,268,944 | B1 | 7/2001 | Szapiel | 359/159 |
| 6,504,971 | B1 | 1/2003 | Margalit et al. | 385/24 |
| 6,522,469 | B1 | 2/2003 | Fuqua et al. | 359/578 |
| 6,545,739 | B1 | 4/2003 | Matsumoto et al. | 349/198 |
| 2002/0191268 | A1 | 12/2002 | Seeser et al. | |
| 2003/0011760 | A1 * | 1/2003 | Vaez-Iravani et al. | 356/237.2 |
| 2003/0048985 | A1 | 3/2003 | Hulse | |

OTHER PUBLICATIONS

William S. Heaps et al., "Fabry-Perot Interferometer for Column $CO_2$," NASA Goddard Space Flight Center, undated, 6 pages.

E. Serabyn et al., "Dual Fabry-Perot Filter for Measurement of CO Rotational Spectra: Design and Application to the CO Spectrum of Venus," *Applied Optics*, vol. 39, No. 34 (Dec. 1, 2000), pp. 6448-6452.

Jerzy Closek, "Narrow-Band Interference Filters with Unconventional Spacer Layers," *Applied Optics*, vol. 39, No. 1 (Jan. 1, 2000), pp. 135-140.

P.L. Land et al., "High-Transmission Comblike Optical Filters," *J. Opt. Soc. Am. A.* vol. 12, No. 3 (Mar. 1995), pp. 611-622.

\* cited by examiner

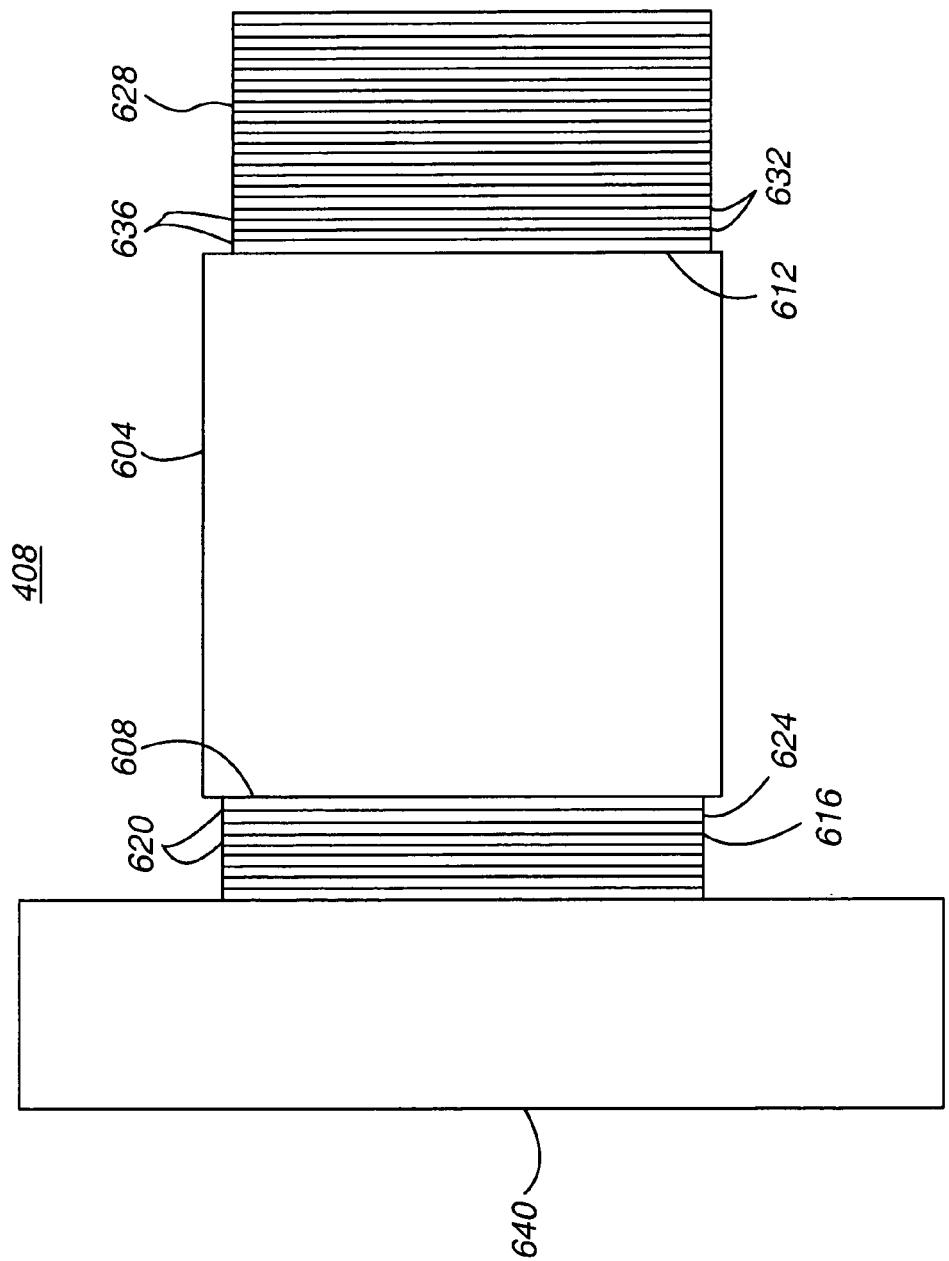

FIELD CONDENSING IMAGING SYSTEM FOR REMOTE SENSING OF ATMOSPHERIC TRACE GASES

CROSS REFERENCE TO RELATED APPLICATIONS

The present application is related to U.S. patent application Ser. No. 10/634,103, filed Aug. 1, 2003, entitled "Method and Apparatus for Providing a Gas Correlation Filter for Remote Sensing of Atmospheric Trace Gases," the entire disclosure of which is incorporated by reference herein in its entirety.

FIELD OF THE INVENTION

The present invention relates to the remote sensing of atmospheric trace gases. In particular, the present invention provides a field condensing imaging system to provide increased accuracy in the measurement of atmospheric trace gases over a relatively wide field of view.

BACKGROUND OF THE INVENTION

The remote sensing of atmospheric trace gases is of increasing importance. In particular, obtaining accurate measurements of atmospheric trace gas species, such as CO and $CO_2$, from an aircraft or spacecraft platform is essential for improving the scientific understanding of global atmospheric chemistry, climate impacts, and the atmospheric component of the global carbon budget.

In order to perform such remote sensing, Fabry-Perot interferometers and other types of high spectral resolution instruments such as Fourier transform spectrometers and grating spectrometers have been identified. In addition, airborne Fabry-Perot instruments have been tested, and measurements from space-based platforms have been proposed. However, the field of view over which a Fabry-Perot interferometer can provide accurate measurements has been limited. Because of this limited field of view, such devices have generally required a scanning mechanism to provide appreciable field coverage. The introduction of a scanning mechanism reduces scan efficiency, which leads to reduced signal integration time, therefore requiring relatively large aperture sizes in order to provide a given signal to noise ratio. This limits the number of spectral samples taken of any one portion of the atmosphere within the field of view of the device and has hindered the wide acceptance of Fabry-Perot interferometers for space-based remote sensing missions.

These limitations of Fabry-Perot interferometers and other optical cavity interference filters are fundamental. The transmission function of the Fabry-Perot interferometer, and derivative optical cavity filters, is a function of the optical path through the etalon cavity. In particular, the wavelengths at which passbands of the Fabry-Perot etalon cavity are formed are highly dependent upon the angle at which collected light has passed through the filter. Specifically, as the angle of incidence of light with respect to the filter changes, the path length of that light through the filter cavity or cavities also changes. The result is a shift in the transmitted wavelengths. Because of this shift, it has been necessary to collect light provided to the filter from over a relatively narrow field of view (e.g., less than 0.2 degrees) in order to prevent the passbands of the filter from moving off of wavelengths corresponding to the spectral lines of absorption of a gas being measured.

In order to perform remote sensing over a wide area, a sensor incorporating a spectrometer device such as the Fabry-Perot interferometer or a thin-film filter can be deployed as part of a moving platform. The forward motion of the platform provides the spatial coverage of the scene, while the spectrometer defines the spectral coverage. Alternatively or in addition, the device can be mechanically scanned. As yet another approach, the index of refraction and/or the spacing between the opposing mirrors forming a Fabry-Perot interferometer can be adjusted or the angle of the etalon filter can be adjusted with respect to the incoming light to provide wavelength scanning. However, each of these approaches requires the instrument to dwell over a fixed location on the ground for a period to provide the wavelength scanning of a fixed scene. These approaches are not capable of providing increased signal integration times nor increased signal to noise ratios when continuous ground coverage is desired. Furthermore, approaches that rely on mechanical adjustments to the etalon are unreliable and are difficult to implement.

SUMMARY OF THE INVENTION

The present invention is directed to solving these and other problems and disadvantages of the prior art. In accordance with an embodiment of the present invention, a field condensing anamorphic telescope is used to provide nearly collimated light in one plane at the entrance to the etalon or correlation filter. Such an optical system provides a magnification that is less than one in at least a first plane. Accordingly, light received by the telescope optical system at a first angle in at least one plane can be provided to a Fabry-Perot interferometer or etalon, or to a multiple cavity optical filter, at a second angle that is less than the first angle.

In accordance with an embodiment of the present invention, the magnification of received light by a factor of less than one is performed in one plane only. This allows, for example, the field angle of received tight to be compressed in a direction that is transverse to the direction of travel of a device platform (i.e., in a cross-track direction), to maintain the passband or passbands of the filter about wavelengths corresponding to absorption lines of the gas being measured. Accordingly, the operative field of view of such an embodiment is increased in a cross track direction. Such an embodiment does not condense the angle of light received at an angle within a plane corresponding to an along-track direction, and therefore provides a wavelength-shifted transmission response by the filter with respect to such light. By thus allowing the passbands of the filter to move away from wavelengths that are centered on the spectral lines of absorption in an along-track direction, measurements of narrowly defined wavelength intervals can be performed at different points along the absorption line wing associated with the lines of absorption. Thus, due to the pressure broadening of absorption lines, information regarding the altitude distribution of the trace gas of interest can be determined.

In accordance with still another embodiment of the present invention, a device that includes a telescope optical assembly that magnifies received fight symmetrically is provided. In particular, a telescope optical assembly having a magnification of less than one with respect to any light received from within the field of view of the device can be provided. By compressing the angle at which collected fight is incident on a filter for fight received from anywhere within the field of view of the device, the filter performance can be reliably maintained over the entire field of view. Such an embodiment is particularly useful in connection with geosynchronous or geo-stationary remote sensing applications. Furthermore, such an embodiment can be combined with tilt scanning of the filter, in order to perform spectral scanning, thereby allowing altitude information regarding atmospheric gases or information regarding different gases in the atmosphere to be obtained.

BRIEF DESCRIPTION OF THE DRAWINGS

FIG. 6 depicts a correlation filter in accordance with an embodiment of the present invention;

DETAILED DESCRIPTION

Figure 1:
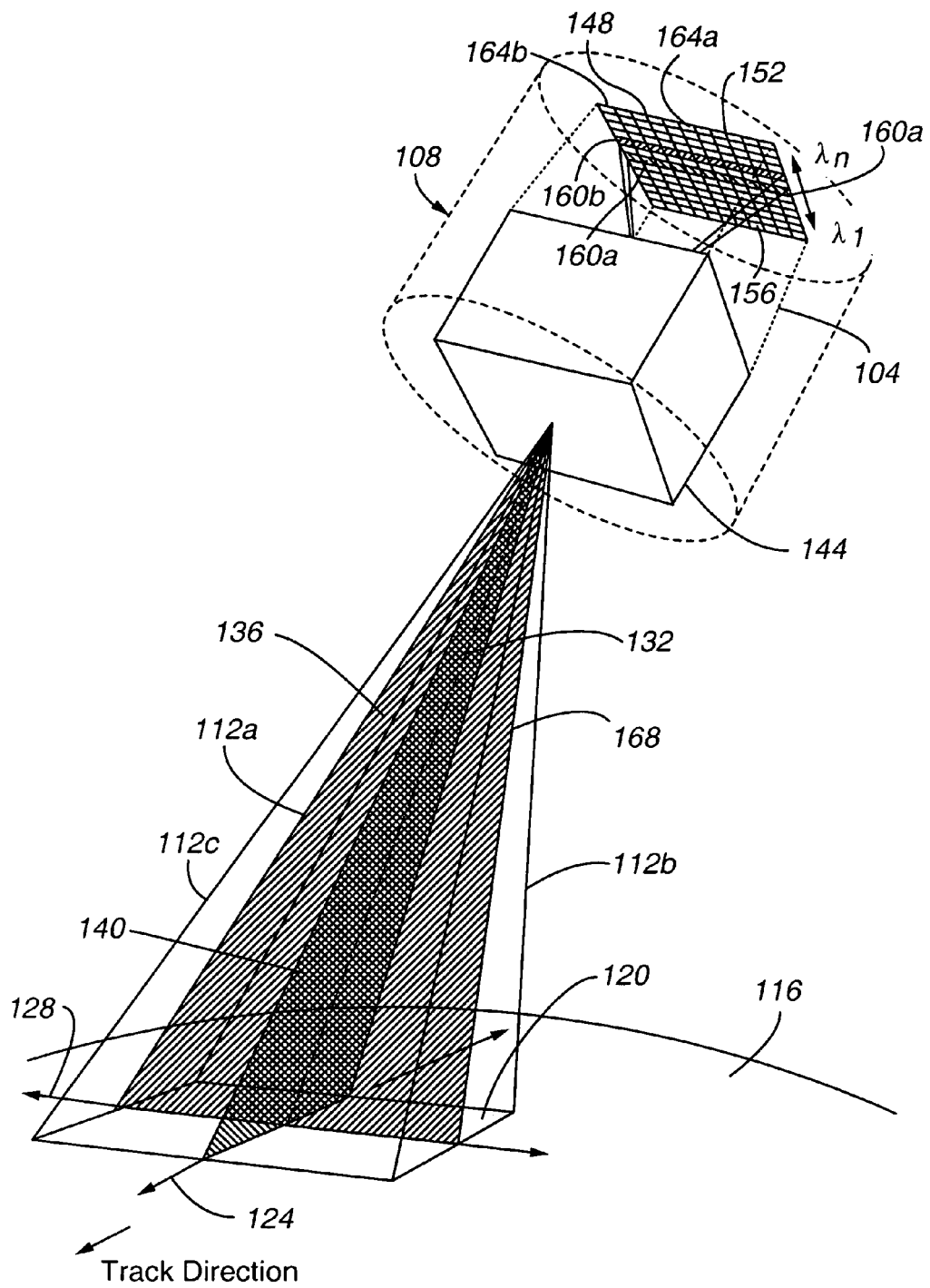
FIG. 1 depicts an arrangement for sensing atmospheric trace gases in accordance with an embodiment of the present invention.

FIG. 1 depicts an arrangement for sensing atmospheric trace gases in accordance with an embodiment of the present invention. The arrangement includes an atmospheric trace gas sensor system 104 in accordance with an embodiment of the present invention, mounted to a platform 108. In general, the platform 108 positions the atmospheric trace gas sensor system 104 such that light may be gathered from a desired portion of the atmosphere. Accordingly, the platform 108 associated with the sensor system 104 may comprise a satellite, such as a geostationary or low-Earth orbiting satellite, as depicted in FIG. 1. In addition, the platform 108 may comprise an aircraft. In accordance with a platform 108 implemented as a satellite or aircraft, the sensor system 104 is typically positioned such that samples of light (depicted as segments 112a–c in FIG. 1) are taken by looking down towards the surface of the Earth 116 as the platform 108 moves in the track direction 124 with respect to the Earth 116 and/or as the sensor system 104 is scanned. In accordance with other embodiments of the present invention, the platform 108 may be positioned on or near the surface of the Earth 116, in which case the sensor system 104 may be oriented such that light is gathered from above or adjacent to the sensor system 104. The span or range of angles over which light can be obtained in connection with sensing a trace gas concentration at an instant in time defines the field of view 120 of the sensor system 104. As will be described in greater detail herein, the sensor system 104 filters collected light, so that the intensity of light at a wavelength or wavelengths corresponding to one or a number of spectral lines of absorption of an atmospheric trace gas of interest can be measured. The measured intensity of the light can then be used as an indication of the quantity of the atmospheric gas of interest within the atmosphere.

The platform 108 may, as noted above, move with respect to the surface of the Earth 116, as represented by line 124. As can be appreciated by one of skill in the art, line 124 illustrates the along-track direction. Line 128 represents a cross track direction. The axis or center of the field of view 132 of the sensor system 104 coincides with an angle of incidence of zero degrees with respect to the sensor system 104. As can be appreciated by one of skill in the art, light that is received from within the first segment 112a but removed from the center line 132 in a cross track 128 direction will be incident upon the sensor system 104 at an angle within a cross-track plane 136 corresponding to the first segment 112a. As can further be appreciated by one of skill in the art, light received from within the second 112b or third 112c segments is removed from the center line 132 in an along-track direction 124 and is incident on the sensor system 104 at an angle within an along-track plane 140 defined by the center line 132 and the along-track direction 124.

Figure 2:
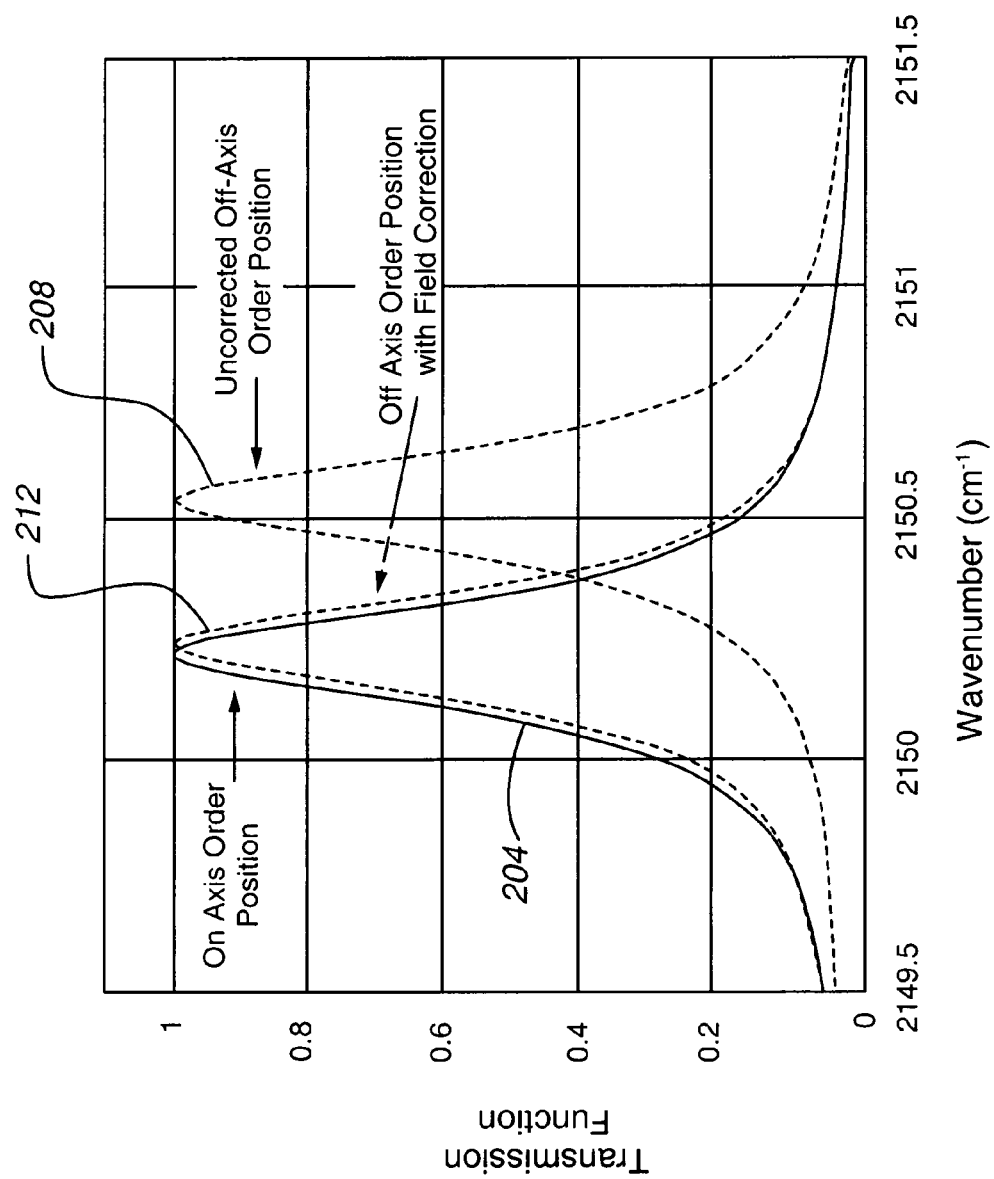
FIG. 2 illustrates the wavelength shift of an ideal interference filter due to an off-axis field angle.

With reference now to FIG. 2, the effect of receiving light at an angle to the axis 132 of the sensor system 104 is illustrated. In particular, line 204 illustrates a transmission function of an interference filter (e.g. filter 408 described elsewhere herein) or Fabry-Perot interferometric filter that might be provided as part of a sensor system 104 in accordance with an embodiment of the present invention, for light received along or parallel to the central axis 132 of the sensor system 104. Line 208 depicts the shift in the position of transmission peak 204 of the filter when light is received at an angle to the axis 132 of a conventional sensor system, or at an angle to the axis 132 of a sensor system 104 in accordance with the present invention in a plane in which the angle of incidence or field angle is not condensed. This shift is the result of a change in the optical path length of a ray through the filter provided as part of the sensor system 104 when the angle of the ray with respect to the filter changes. Line 212 illustrates the shift in the position of the transmission peak 204 for light received at a sensor system 104 in accordance with an embodiment of the present invention at an angle within a plane for which field angle correction or condensation has been applied. For example, line 212 may represent the shift observed with respect to light received at an angle of 4° in a first plane by an optical system 144 that provides about 0.25× magnification in the first plane. For a filter adapted to pass light at a wavelength or wavelengths corresponding to the wavelength of an absorption line or lines of an observed gas, the reduced shift of the transmission peak center wavelength allows the intensity of light having a wavelength corresponding to an absorption line or lines of the observed gas to be measured, even though such light is incident on the filter 408 at an angle. As can be appreciated from the description of the present invention provided herein, a sensor system 104 in accordance with the present invention may provide a condensed field angle in a first plane (e.g., the cross-track plane 136) but not in a second plane (e.g., along-track plane 140). In accordance with still another embodiment of the present invention, field angle correction may be provided symmetrically about the central axis 132 of the sensor system 104.

With reference again to FIG. 1, the sensor system 104 includes an optical system 144 and a detector array 148 comprising a two-dimensional array provided as part of a detector assembly 152. In particular, FIG. 1 illustrates that light received from within different segments 1112 (or from different angles within the along-track plane 140) are incident upon pixels 156 in different rows 160 of the detector array 148. For example, a ray of light received from within the first segment 112a will be incident upon a pixel 156 included in a first row 160a of pixels 156, while a ray of light received from within the second segment 112b will be received at a pixel 156 included in a second row of pixels 160b. Furthermore, it should be appreciated that light received from within the first segment 112a is, in the exemplary embodiment depicted in FIG. 1, received by the optical system 144 at an angle of 0° to the axis 132 in the along-track plane 140, and therefore has an angle of 0° in the along-track plane 140.

FIG. 1 also illustrates that light rays at different angles within the cross track plane 136 are received by pixels 156 located in different columns 164 of the detector array 148. For example, light received at an angle of 0° to the axis 132 in the cross track plane 136 (for example, a ray of light received from along the axis 132 of the sensor system 104) is incident upon a pixel 156 included within a first (or central) column 164a of pixels 156 included in the detector array 148. Light received at an angle with respect to the axis 132 in the cross track plane 136 (for example, light received from along an edge of the first segment 112a, such as from along ray 168) is received at a second column 164b of pixels 156.

As noted above, field angle correction or condensation allows the transmission peak of an interference filter to be maintained about a spectral line of absorption associated with an atmospheric gas. Accordingly, the amount or concentration of a gas in the atmosphere can be accurately detected and measured for ground pixels (i.e., columns of the atmosphere that are imaged on a pixel 156 of the detector array 148) anywhere within the field of view 120, even if the sensor system 104 gathers light from within a relatively large field of view 120. This allows information regarding the total amount of a gas within the observed column to be determined. Accordingly, large volumes of the atmosphere can be observed at the same moment or period of time. As can also be appreciated, in an embodiment of the present invention that allows the field angle to cause a shift in the transmission peak or peaks in an along-track direction 124, measurements of the concentration of trace gas along the absorption line wing associated with that trace gas can be taken since the transmission peak or peaks are shifted with the ray angle within the filter. Because of the effect of pressure broadening, this allows information regarding the height distribution of an atmospheric gas to be obtained. In particular, in a pushbroom type arrangement, the spectral sampling along the line wing occurs at different ground locations in the along-track (i.e., flight) 124 direction. Accordingly, the same imaged ground pixel is sequentially spectrally sampled in time as the platform 108 moves in the along-track direction 124, allowing the height or altitude distribution of the gas of interest to be constructed during on-board or ground processing.

Figure 3:
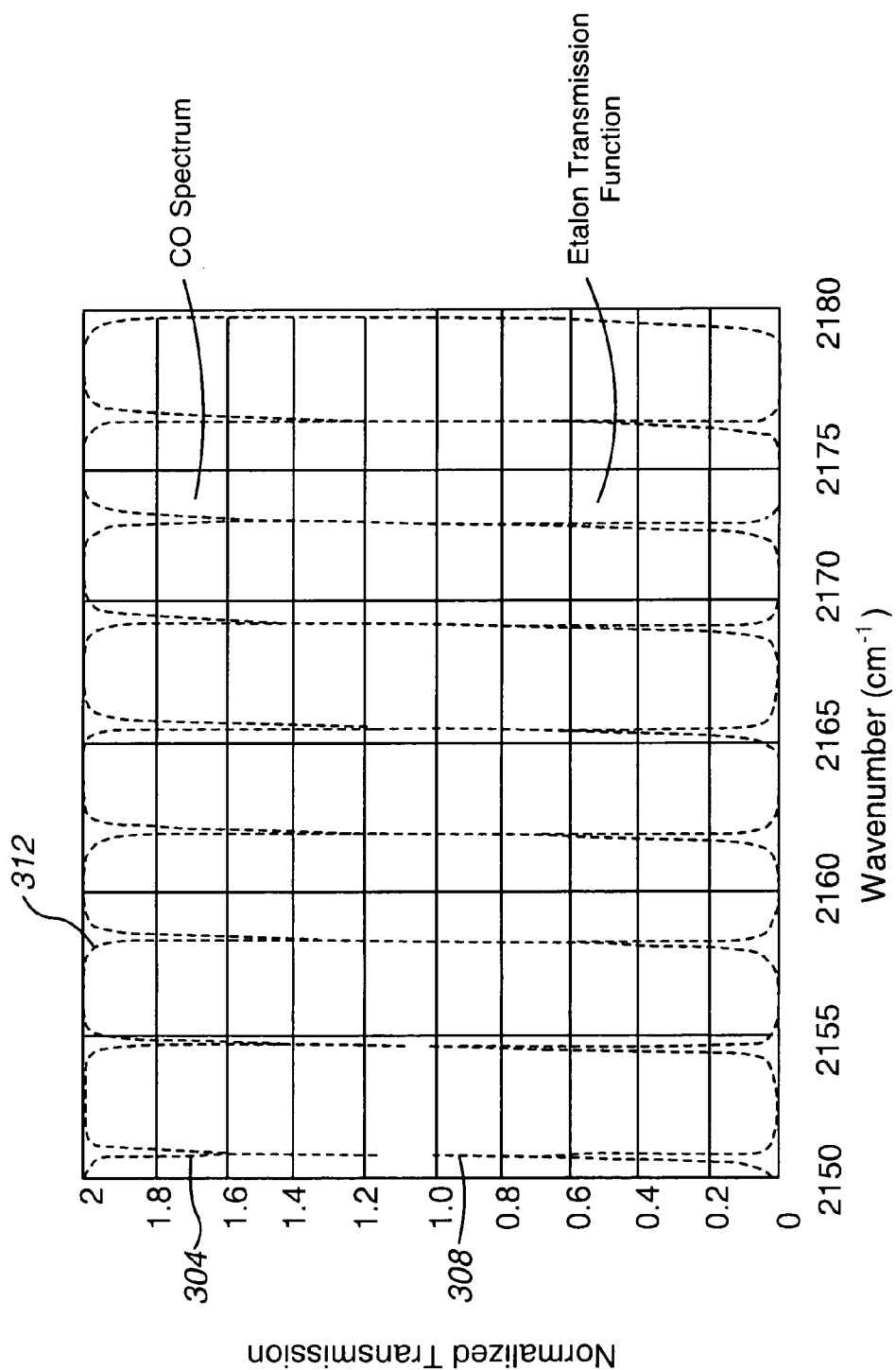
FIG. 3 illustrates the relationship between the spectral lines of absorption associated with an atmospheric gas and the passbands of a sensor device in accordance with an embodiment of the present invention.

With reference now to FIG. 3, absorption lines 304 associated with Carbon Monoxide, which is an example of an atmospheric trace gas, are shown. Also shown in FIG. 3 are passbands 308 of a sensor system 104 in accordance with an embodiment of the present invention incorporating a novel correlation filter 408 (see, e.g., FIGS. 6 and 8 and the accompanying description) that allows each of the nine passbands 308 illustrated in FIG. 3 to be centered on or include an absorption line 304 center wavelength. As noted above, by compressing or limiting the field angle of collected light in at least a cross track 128 direction, the alignment of the passbands 308 with respect to the absorption lines 304 can be maintained for each pixel 156 in a row 160.

In accordance with an embodiment of the present invention that does not compress field angle with respect to an along-track 124 direction, the center wavelengths of the transmission peaks 308 will shift with field angle in the along-track 140 plane. Because the magnitude of the shift increases with angle, the wavelength at which each transmission peak is centered will walk along the line wing 312 of the absorption spectrum for the gas, away from the center wavelength of the absorption line 304, as the angle increases. As can be appreciated by one of skill in the art, different positions along the line wing 312 correspond to the absorption due to the gas of interest at different altitudes within the atmosphere. In particular, in the case of a downlooking sensor, the center wavelength of each absorption line 304 provides information regarding the total amount of the trace gas within the observed column. Moving along the line wing 312, away from the center wavelength, information regarding the concentration of the trace gas can be obtained for progressively lower altitudes. Thus, in such an embodiment, each column 164 of pixels 156 in the detector array 148 provides information regarding a different column of atmosphere overlying a different ground pixel, while each row 160 of pixels 156 provides information regarding the concentration of the gas being measured at a different altitude for each imaged ground pixel.

Figure 4:
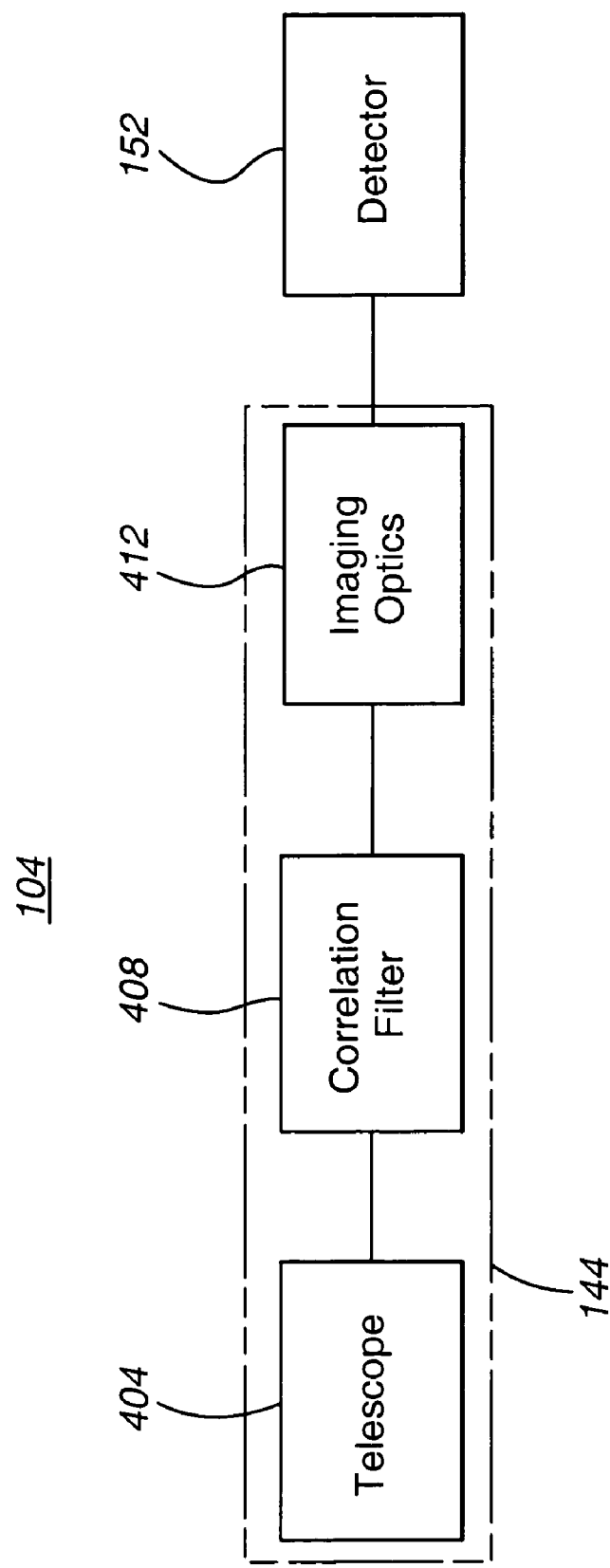
FIG. 4 is a block diagram depicting components of an atmospheric trace gas detection system in accordance with an embodiment of the present invention.
Figure 18:
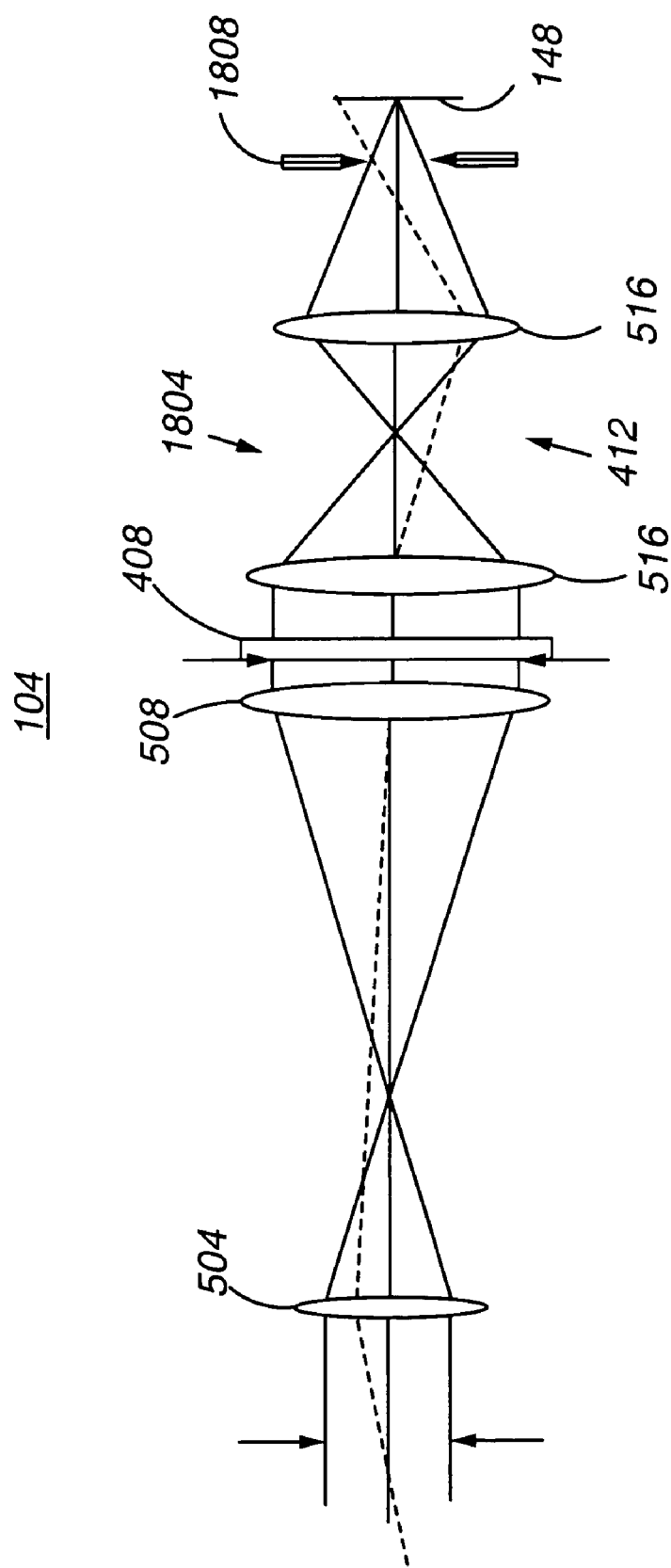
FIG. 18 is a schematic depiction of components of a system for detecting atmospheric trace gases having a cold stop in accordance with an embodiment of the present invention.

With reference now to FIG. 4, a block diagram depicting a sensor system 104 in accordance with an embodiment of the present invention is shown. In general, the sensor system 104 includes a telescope optical system 404, a passband filter 408, and an imaging lens group 412, provided as part of the optical system 144, and a detector assembly 152. As depicted in FIG. 18, the imaging lens group 412 may include a relay assembly 1804 such that the system entrance pupil is reimaged onto a detector assembly cold stop 1808, thereby providing 100% or near 100% cold stop efficiency. As can be appreciated by one of skill in the art, the cold stop 1808 may comprise a field of view limiting aperture that is cyrogenically cooled to prevent background radiation from reaching the detector array 148.

The telescope optical system or telescope 404 may generally comprise an optical system for gathering light over a selected field of view 120 (see FIG. 1). Furthermore, the telescope 404 may function to provide collimated or nearly collimated light to the passband filter 408. In accordance with an embodiment of the present invention, and as will be described in greater detail herein, the telescope 404 provides field angle compression, to limit the angle of incidence of light on the passband filter 408. This field angle compression may be performed with respect to light received at an angle to the axis 132 of the sensor system 104 within the cross track plane only 136, or with respect to light received at an angle to the axis 132 of the sensor system 104 within both the cross track 136 and along-track 140 planes.

Figure 5A:
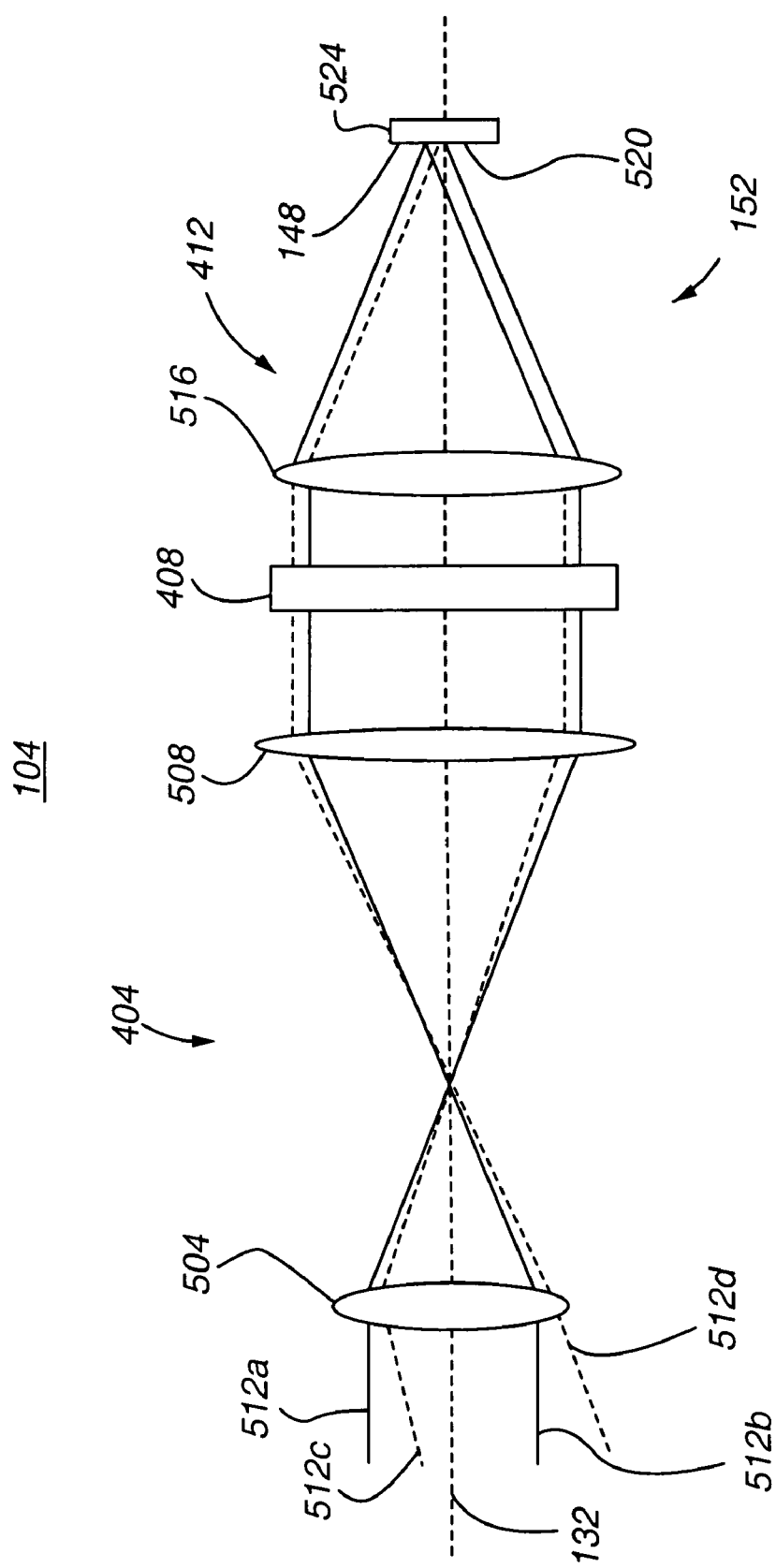
FIG. 5A is a schematic depiction of components of a system for detecting atmospheric trace gases in the crosstrack direction in accordance with an embodiment of the present invention.

With reference now to FIG. 5A, components of the sensor system 104 in accordance with an embodiment of the present invention are depicted schematically in a section taken along a first plane. In particular, the telescope optical system 404 is illustrated as including an objective lens 504 for collecting light from a volume that comprises the field of view 120 of the sensor system 104. In addition, the telescope optical system 404 is shown as including a rear imaging element or lens 508. Rays 512 illustrating some possible paths of light through the sensor system 104 are also shown. As can be appreciated from the depiction of the lenses 504, 508 of the telescope optical system 404, and from the rays 512 shown passing through the sensor system 104, the telescope optical system 404 may comprise refracting elements that deliver collimated or nearly collimated light to the passband filter 408. As used herein, nearly collimated light means light that is at least within several degrees of being perfectly collimated. Although FIG. 5A depicts the telescope optical system 404 as a refractive type device, other telescope designs can be used. For example, an all reflective design or a combination reflector and refractor (catadioptic) design may be used. In addition, diffractive elements may also be employed.

The telescope optical system 404 functions to compress the field angle of light received from within the field of view 120 at an angle to the axis 132 of the sensor system 104 within at least the first plane. In particular, the telescope 404 is an afocal telescope having a magnification of less than 1.0 within at least the first plane. The effect of magnifying light received at an angle to the axis 132 of the sensor system 104 by less than 1.0 is to compress or reduce the angle of such light with respect to the filter 408. This effect is illustrated in FIG. 5A. In particular, rays 512c and 512d are shown entering the sensor system 104 at an angle of about 10° to the central axis 132. However, due to the magnification of the telescope optical system 404 in the plane within which the rays 512c and 512d are at an angle to the axis 132 of the sensor system 104, that angle is reduced to about 1° at the filter 408. Accordingly, FIG. 5A illustrates a telescope optical system 404 with a magnification or optical power of about 0.1. Rays 512a and 512b are parallel to the axis 132 of the sensor system 104. Because they are at an angle of 0° to the axis 132 of the sensor system in the illustrated plane, they are not affected by the magnification of the telescope optical system 404, and remain parallel to the central axis 132 when they reach the filter 408.

As noted above, by correcting or at least limiting the angle at which light is incident upon the filter 408, the transmission peaks of the filter 408 can be maintained at or at least including a desired center wavelength, at least up to some maximum angle of incidence. In an additional aspect of embodiments of the present invention, the filter 408 includes a cavity or etalon formed from material having a relatively high index of refraction. By providing a filter 408 having an optical cavity or etalon comprising a material having relatively high index of refraction, the angle within the cavity can be reduced from the angle at which the light is incident on the filter 408. Accordingly, the change in path length experienced by a ray received at an angle to the filter 408 can be reduced in the filter 408, thus further limiting the shift in the wavelength of the filter's 408 transmission peak or peaks. For example, fight at an angle of about 1° to the surface of the filter 408 can be reduced to within 0.2° within the filter 408 if the optical cavity or cavities are formed from a material having a relatively high (e.g., n>2.0) index of refraction. Additional aspects of the filter 408 in accordance with embodiments of the present invention will be described in greater detail elsewhere herein.

The detector assembly 152 receives the filtered light from the filter 408. As depicted in FIG. 5A, the sensor system 104 may include imaging optics 412 comprising a focusing lens or lenses 516 that function to focus the fight received from the filter 408 onto the surface 520 coinciding with the detector array 148 of a detector element 524. As can be appreciated by one of skill in the art, the detector element 524 may comprise a phototransducer. For example, the detector element 524 may comprise a charge coupled device (CCD), photocathode, or photodiode. Because the fight received at the detector element 524 has been filtered so that only wavelengths corresponding to absorption lines of a gas being measured (i.e., the target gas) are received, the intensity of the fight at the detector element 524 provides an indication of the amount of that gas within the field of view of the sensor system 104. Furthermore, the intensity of the light at a pixel 156 (see FIG. 1) of the detector assembly 152 provides an indication of the amount of the gas within the column of the atmosphere corresponding to that pixel 156. In particular, information regarding a total amount of the gas in the observed column of the atmosphere is obtained for a column of the atmosphere along a ray that is at about 0° to the filter 408, whether because it is along or parallel to the axis 132 of the sensor system 104, or because the angle of the ray associated with the column of the atmosphere has been corrected or condensed. In accordance with a further embodiment of the present invention, the sensor system 104 may comprise a cold stop 1808, as depicted in FIG. 18, to prevent background radiation from outside of the active area of the sensor 104 from affecting the measurements.

In an embodiment of the present invention in which the telescope optical system 404 provides field angle correction or compression in both the cross-track 136 and along-track 140 planes, FIG. 5A schematically depicts a section of the sensor system 104, whether that section is in the cross-track plane 136 or the along-track plane 140. Accordingly, the same spectral response can be maintained for light gathered from anywhere within the field of view 120. Such an embodiment, in which symmetrical optical power is provided, may be used in connection with, for example, a geostationary or geosynchronous satellite platform 108 to produce a two-dimensional image of gas concentration within the field of view 120 of the sensor system 104. Spectral sampling in connection with such an embodiment can be accomplished by tilt-scanning the filter 408.

Figure 5B:
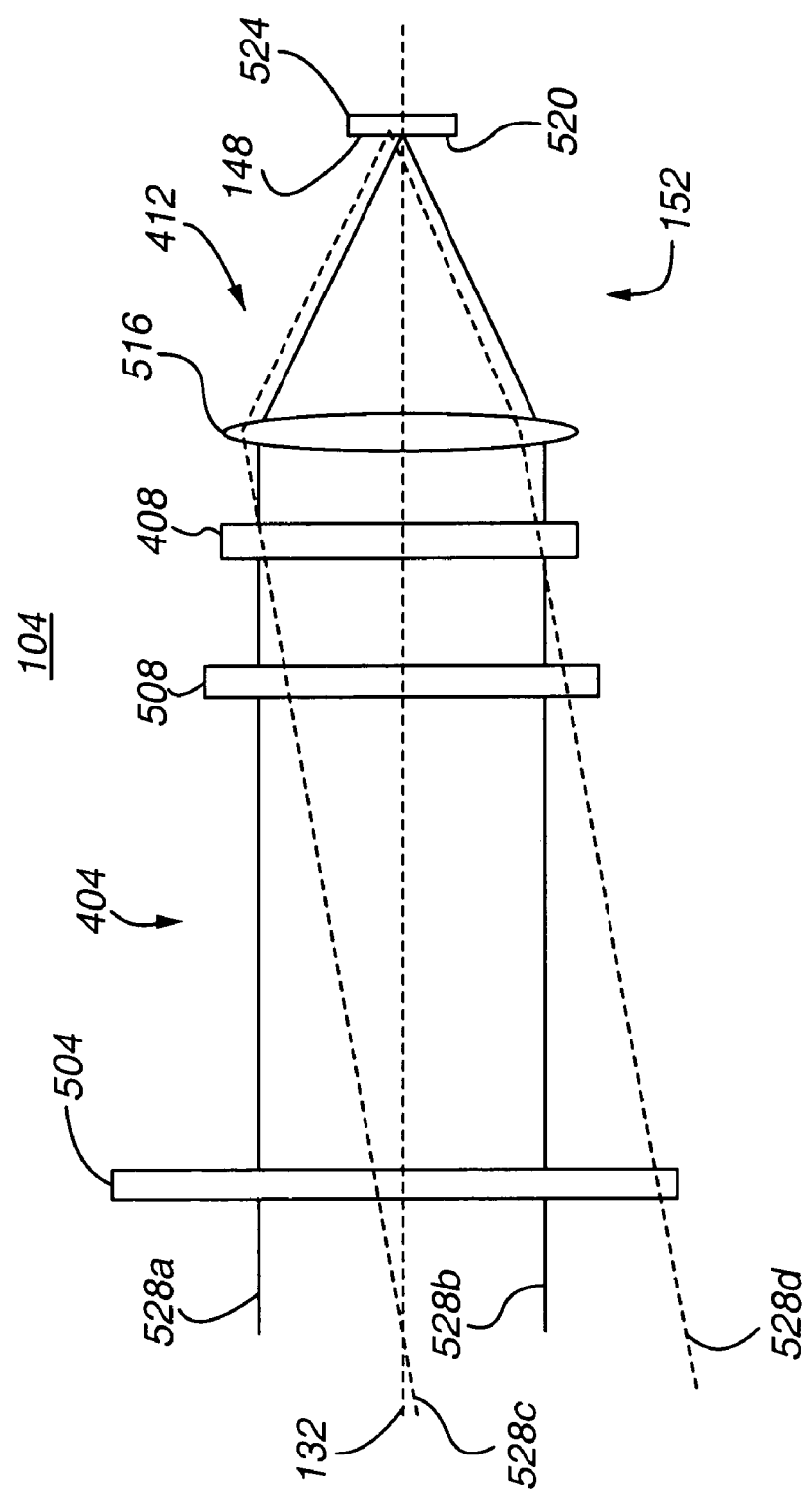
FIG. 5B is a schematic depiction of components of a system for detecting atmospheric trace gases in the alongtrack direction in accordance with an embodiment of the present invention.

In accordance with a further embodiment of the present invention, the sensor system provides field angle correction or compression in only one plane. In connection with such an embodiment, FIG. 5A schematically depicts a section of the sensor system 104 that is in a plane in which such field angle correction or compression is provided, and FIG. 5B schematically depicts a section of such an embodiment of a telescope optical system 404 in a plane in which there is no optical power. For example, FIG. 5B may depict a section of the sensor system 104 that is in the along-track plane 140. Thus, FIG. 5A would be a view of the telescope optical system 404 illustrated in FIG. 5B but taken from a view rotated 90° from the view in FIG. 5A. Accordingly, taken together, FIGS. 5A and 5B are illustrative of an embodiment of the present invention comprising an anamorphic afocal telescope optical system 404 having no optical power in an along-track 124 direction.

As shown in FIG. 5B, rays 528 that are parallel to the axis 132 of the sensor system 104 in the illustrated plane (e.g., rays 528a and 528b) are passed to the filter 408 without alteration of their angle. Rays that are at an angle to the axis 132 (e.g., rays 528c and 528d) may be passed to the filter 408 without any alteration of that angle. As noted above, such an embodiment, in which asymmetrical optical power is provided, may be used in connection with a moving platform 108 in a pushbroom application to sequentially produce a ground image and its spectrum, so that a profile of the altitude distribution of a gas in a column of the atmosphere can be constructed. In particular, by condensing the field angles in the cross-track 128 direction, the influence of the cross-track field angle on the transmission function of the filter 408 can be eliminated or reduced, thereby maintaining a consistent spectral response for light received at an angle in the cross-track plane 136 and consequently providing a wide field of view 120. By allowing the field angle to increase from the nadir ground location (corresponding to the axis 132 of the sensor system 104) to the edge of the field of view 120 in the along-track direction 124, the field angle dependence of the filter 108 will cause shorter wavelengths to be transmitted. This wavelength shift allows samples from different spectral positions along the absorption line wing to be obtained.

In particular, in accordance with an embodiment of the present invention that provides field angle correction or compression in the cross-track plane 136 only, the wavelength of light passed by the optical system 144 to different rows 160 of pixels 156 will vary. Accordingly, different rows 160 of pixels 156 receive information regarding the concentration of a gas of interest at different attitudes. When such an embodiment is combined with a platform 108 that moves in an along-track direction 124, the same ground pixel (i.e., the pixel or area at the surface of the Earth 1116 and the atmospheric column above it that is imaged on a pixel 156 of the array 148) can be sequentially spectrally sampled by each of the pixels 156 in a column of pixels 164, allowing an altitude distribution of the gas of interest to be constructed.

In accordance with an embodiment in which field angle correction is provided symmetrically in both the cross-track 136 and along-track 140 planes, each pixel 156 of the array may be provided with light at or about the same wavelengths. As used herein, about the same wavelength means that the center wavelength of the effective passband or passbands of the filter with respect to any one pixel 156 is shifted no more than 0.05 cm$^{-1}$ from the passband or passbands of any other pixel 156. Such an embodiment therefore functions to correct the circular fringe pattern or "spectral smile" of an optical interference filter to which light is provided from over a wide field of view 120. Furthermore, such an embodiment is particularly useful in connection with a staring array sensor. If altitude information regarding the gas of interest is desired in connection with such an embodiment, it can be obtained by tilt scanning the filter, thereby shifting the filter passband or passbands.

With reference now to FIG. 6, a passband filter comprising a multiple-peak correlation filter 408 in accordance with an embodiment of the present invention is schematically depicted. As shown in FIG. 6, such an embodiment includes an optical cavity or etalon 604 formed between a first or reflecting surface 608 mirror at a first surface of the etalon 604 and a second mirror or reflecting surface 612 at a second surface of the etalon 604. As can be appreciated by one of skill in the art, the etalon 604 may comprise a Fabry-Perot interferometer or etalon. The etalon 604 has an optical thickness corresponding to a number (e.g., 10 or more) of wavelengths of light having a wavelength corresponding to a passband of the filter 408. In accordance with an embodiment of the present invention, the etalon 604 comprises a Silicon or Germanium etalon. For example, in connection with a filter 408 for use in sensing the presence of CO in the atmosphere, the etalon 604 may be formed from a 386.5 μm thick piece of Silicon. In accordance with a further embodiment of the present invention, the etalon 604 may be formed from a piece of material having a diameter of greater than about 5 centimeters. In accordance with still another embodiment of the present invention, the etalon 604 may have a diameter of greater than 8 centimeters. The high refractive index of silicon (for which n=3.42) reduces the sensitivity of the filter 408 to field angle, thereby producing a larger useful field of view than an etalon 604 in which the light passes through a low refractive index cavity, such as a vacuum or air. Although an etalon 604 having a relatively high index of refraction provides certain advantages, it should be appreciated that embodiments of the present invention may include an etalon having a low index of refraction, such as air. In addition, the relatively large diameter assists in providing a relatively large effective field of view.

The first reflective surface 608 of the etalon 604 may be formed on or defined by a first multi-layer reflective coating stack 616. The multi-layer reflective coating stack 616 may be formed from alternating layers of high and low index of refraction material. In particular, the reflective stack 616 may be formed from the alternate layering of films having a low index of refraction 620 with films having a high index of refraction 624. In accordance with an embodiment of the present invention, the films or layers of low refractive index material 620 are formed from Silicon Monoxide (SiO) and the high index of refraction layers 624 are formed from Germanium (Ge). In accordance with another embodiment of the present invention, high index of refraction layers 624 formed from Ge are combined with low index of refraction layers 620 formed from Silicon Dioxide ($SiO_2$). Different numbers of thin film layers may be applied to form the reflective stack 616. For example, a three layer stack 616 following the coating formula HLH (where H indicates a high index of refraction layer 624, and where L indicates a low index of refraction material 620) may be used. In accordance with another embodiment of the present invention, a greater number of layers may be applied. For example, the reflective stack 616 may comprise a coating formula described as $(HLH)^3$. Each of the layers 620, 624 of the reflective stack 616 may be formed by depositing successive layers of the material on the first surface 608 of a silicon etalon 604.

The second reflective surface 612 may be formed from a second multi-layer reflective coating stack 628 that comprises alternating layers of high refractive index 632 and low refractive index 636 thin film layers. Furthermore, embodiments of the present invention may include a second multi-layer reflective coating stack 628 that comprises a correlation stack. In a stack 628 comprising a correlation stack, at least some of the layers of high 632 and low 636 refractive index material have non-quarter wave optical thicknesses. That is, the thickness of at least some of the layers 632, 636 is not equal to one quarter of a wavelength of light corresponding to the center of a passband of the correlation filter 608 when traveling through such a layer 632, 636. This feature of the second multi-layer reflective coating or correlation stack 628 allows the spacing of the filter transmission peaks to be altered from peaks having perfectly regular spacing in wavelength to peaks that correspond to the non-periodically spaced absorption lines of an atmospheric gas. More particularly, the thickness of individual layers 632, 636 is chosen to produce a wavelength dependent change in optical path (i.e., phase) and hence a desired change in spacing of the filter transmission peaks.

The correlation stack 628 may include film or layers of Ge to form high index of refraction layers 632 and films or layers of SiO to form low index of refraction layers 636. In accordance with another embodiment of the present invention, the low index of refraction layers 636 may be formed from $SiO_2$ instead of SiO. In general, the exact number of layers 632, 636 and the thicknesses of each of those layers 632, 636 will vary depending on the atmospheric gas whose absorption lines are to be matched by the correlation filter 408. Layers may be added and/or layer thicknesses altered to arrive at the desired passband spacing. As can be appreciated by one of skill in the art, various analytical tools for analyzing and designing optical devices using thin film may be applied in designing the correlation filter 408. In an exemplary embodiment, the correlation stack 628 is formed from about 20 to 30 layers, and has a total stack thickness of 1 to 3 µm. For example, an embodiment of a correlation filter 408 may have a correlation stack 628 with a coating or layer formula of $(HLH)^9$.

As illustrated in FIG. 6, the filter 408 may be formed on or interconnected to a substrate 640. For example, a substrate 640 formed from ZnSe or from Si may be used to facilitate the manufacture and mechanical integrity of the correlation filter 408.

Figure 7:
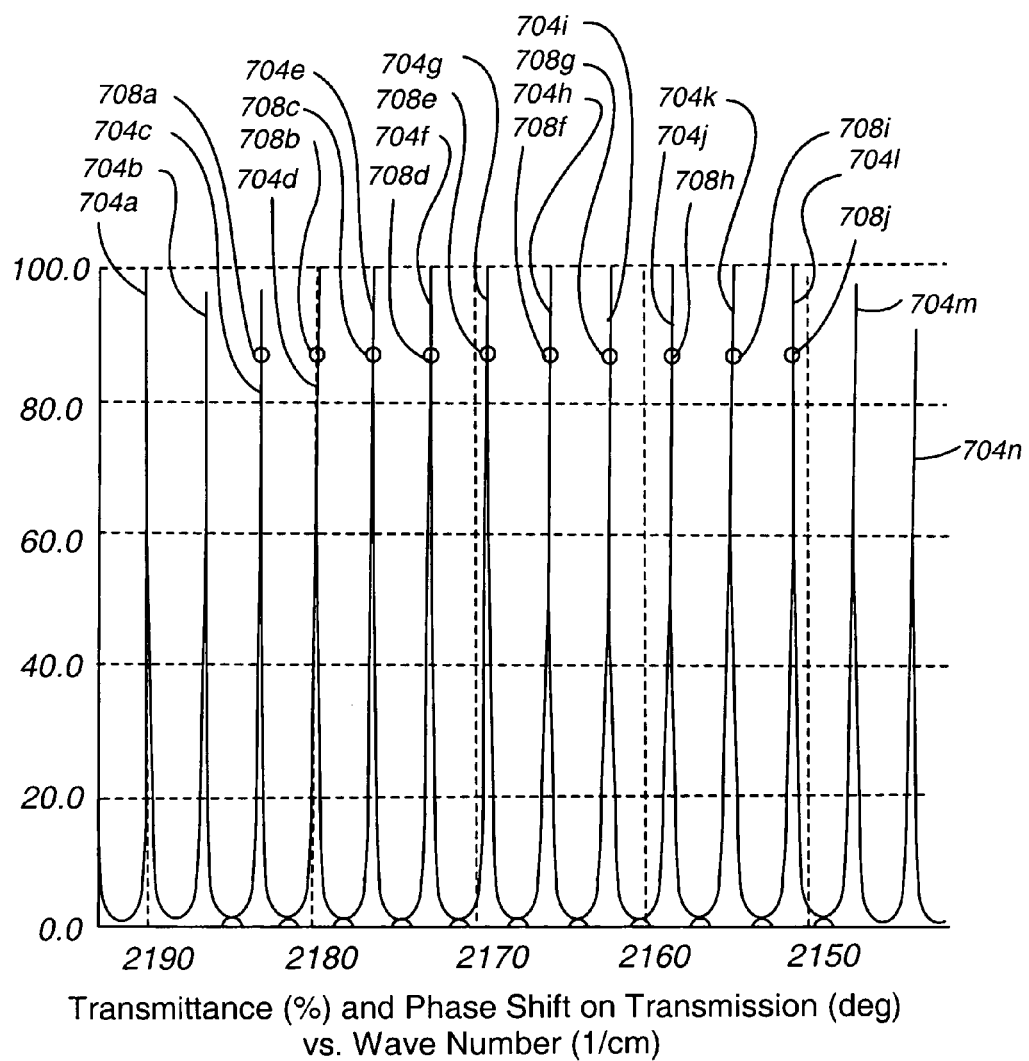
FIG. 7 illustrates the relationship between the passbands of the correlation filter illustrated in FIG. 6 and the spectral lines of absorption of an atmospheric trace gas.

With reference now to FIG. 7, the predicted performance of a filter 408 according to the embodiment of a correlation filter 408 illustrated in connection with FIG. 6 is shown. In FIG. 7, a number of transmission peaks 704a–n can be seen. As can be appreciated from a close inspection of the position of the transmission peaks 704, the spacing between adjacent transmission peaks 704 increases with decreasing wave number (i.e., increasing wavelength). In particular, the filter transmission peaks 704 are spaced such that a relatively large number of the transmission peaks (i.e., transmission peaks 704c–l) correspond to the infrared absorption line positions of CO, denoted by circles 708a–j. Accordingly, it can be appreciated that a correlation filter 408 according to the embodiment illustrated in FIG. 6 can be designed to pass light at wavelengths corresponding to 10 absorption lines associated with CO. Because such a large number of absorption lines 708 are centered within the filter transmission peaks 704, a sensor system 104 utilizing a correlation filter 408 in accordance with the present invention can provide a very high signal-to-noise ratio. In addition, because, as shown in FIG. 7, the transmission peaks 704 are very narrow, a system 104 with very high resolution can be provided. As can be appreciated by one of skill in the art, this correlation filter 408 may be combined with or incorporate a bandpass filter to isolate the ten transmission peaks 704 corresponding to absorption fines 708. As can be appreciated by one of skill in the art, the wavelength of transmission peaks of the associated field condensing imaging system can be selected to correlate to any atmospheric gas.

Figure 8:
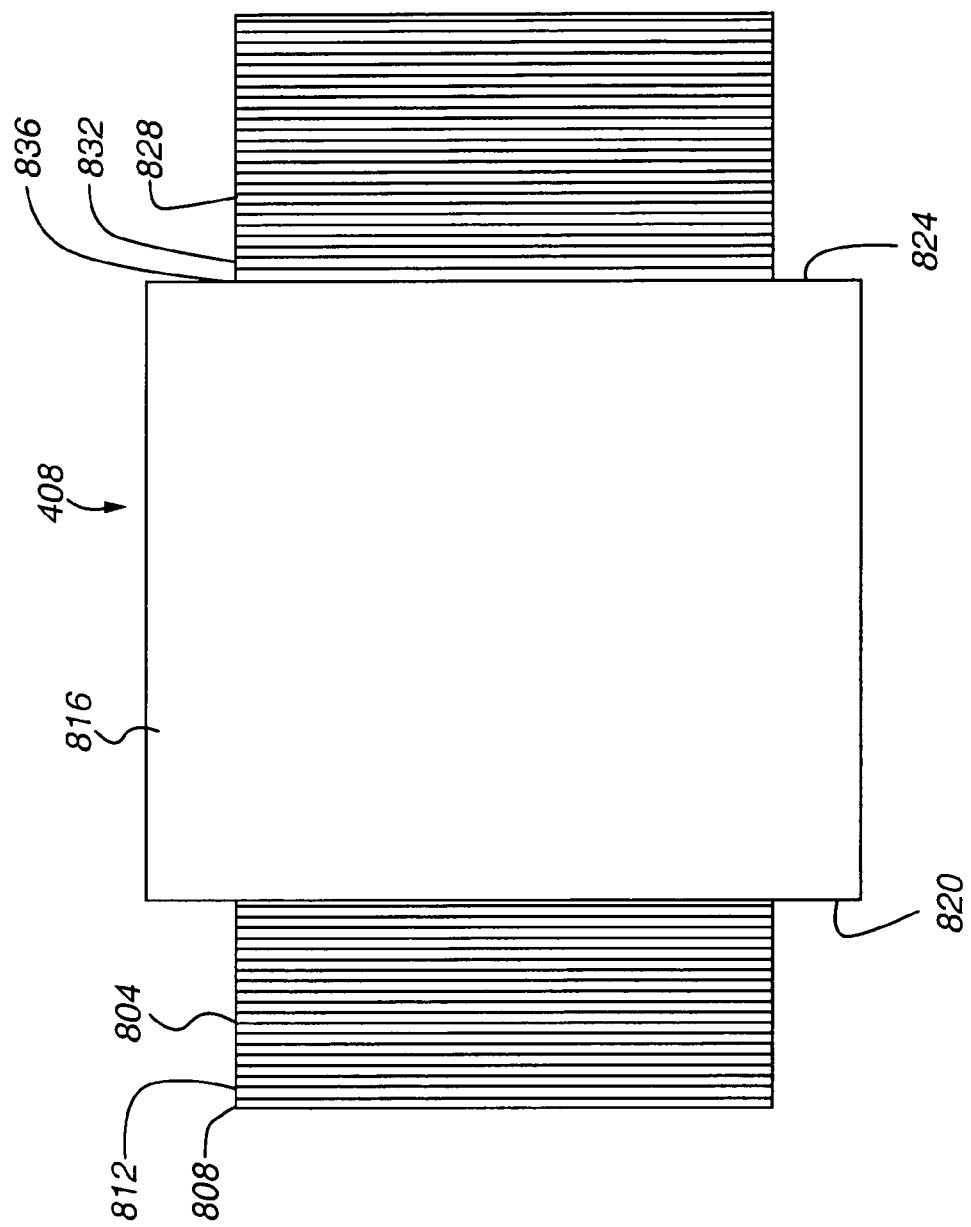
FIG. 8 depicts a correlation filter in accordance with another embodiment of the present invention.

With reference now to FIG. 8, a filter comprising correlation filter 408 in accordance with another embodiment of the present invention is depicted. According to the embodiment shown in FIG. 8, the filter 408 includes a multiple layer compensation stack 804 having layers of high index of refraction material 808 alternating with layers of low index of refraction material 812. In particular, at least some of the high index of refraction layers 808 may comprise high index of refraction cavities, formed from a material such as Ge. The low index of refraction layers 812 may comprise low index of refraction spacers formed from a material such as SiO. At least some of the layers 808, 812 have an optical thickness that does not equal an integer multiple of one quarter of the center wavelength of a passband of the filter 408. By providing non-quarter wave thickness layers 808, 812, the phase compensation stack 804 may provide filter characteristics such that the transmission peaks of the filter 408 are non-periodic. In accordance with an embodiment of the present invention, the phase compensation stack 804 may include a total of 21 thin film layers.

The correlation filter 408 may additionally include a substrate 816. In general, the substrate 816 may provide a surface on which the compensation stack 804 may be formed. In addition, the substrate 816 may provide for the mechanical stability of the correlation filter 408. In accordance with an embodiment of the present invention, the substrate 816 may be formed from Germanium and may have a thickness of about 4 millimeters. In accordance with a further embodiment of the present invention, the substrate 816 may include first 820 and second 824 surfaces lying in planes that are not parallel to one another (i.e., the substrate 816 may be wedged). A wedged substrate 816 prevents the substrate 816 from itself forming an optical cavity and thus an interference type filter.

As also shown in FIG. 8, a correlation filter 408 may include a bandpass filter 828 to isolate the transmission peaks of interest. The bandpass filter 828 may be conventionally formed from alternating layers of high 832 and low 836 refractive index layers having quarter wave thicknesses. For example, the bandpass filter 828 may be formed from alternating layers of Titanium dioxide ($TiO_2$) and Silicon dioxide ($SiO_2$).

Figure 9:
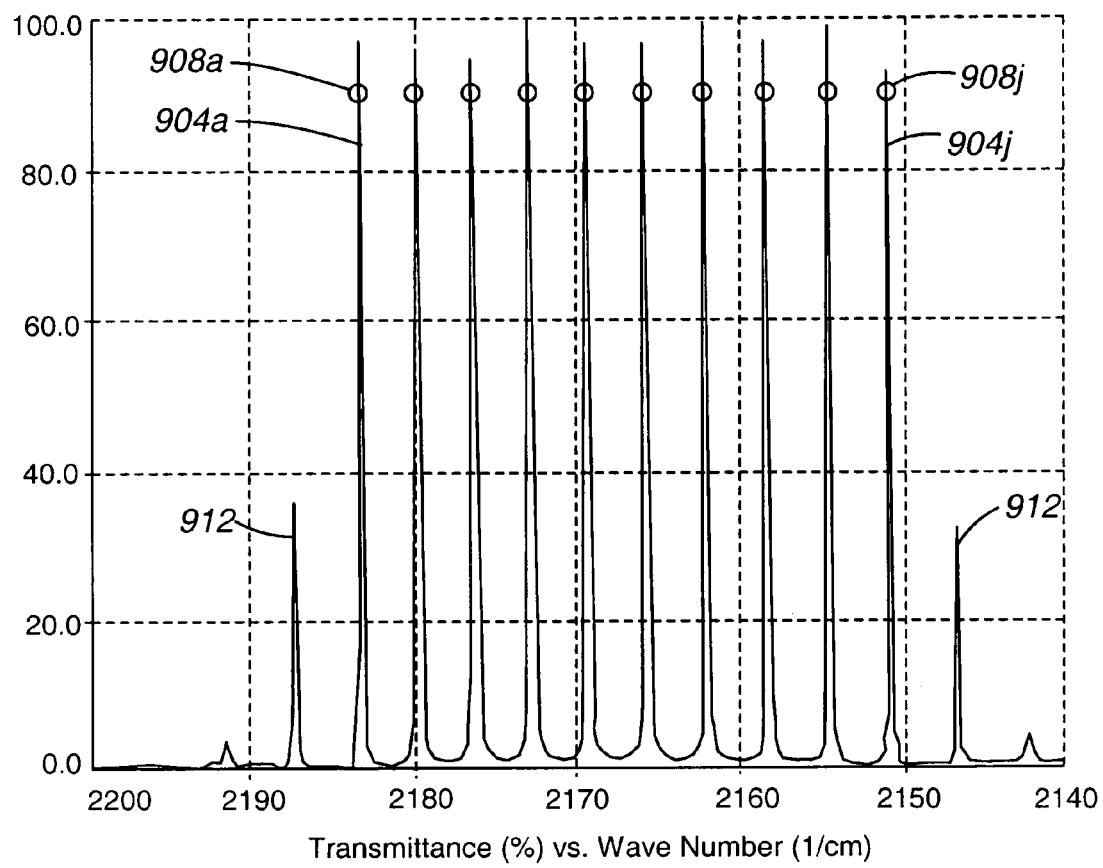
FIG. 9 illustrates the relationship between passbands of the correlation filter illustrated in FIG. 8 and the spectral lines of absorption of an atmospheric trace gas.

With reference now to FIG. 9, the transmission characteristics of a correlation filter 408 as illustrated in FIG. 8 is shown. In particular, the ten major transmission peaks 904a–j corresponding to ten absorption lines of carbon monoxide, indicated by circles 908a–908j, are illustrated. Also shown in FIG. 9 are attenuated transmission peaks 912. Such attenuation results from the use of a bandpass filter 828 to isolate the transmission peaks 904 of interest. As seen in FIG. 9, the transmission peaks of the correlation filter 408 occur at 2190.02 cm$^{-1}$, 2186.64 cm$^{-1}$, 2183.22 cm$^{-1}$, 2179.77 cm$^{-1}$, 2176.28 cm$^{-1}$, 2172.76 cm$^{-1}$, 2169.20 cm$^{-1}$, 2165.60 cm$^{-1}$, 2161.97 cm$^{-1}$, 2158.30 cm$^{-1}$, 2154.60 cm$^{-1}$, and 2150.86 cm$^{-1}$, corresponding to the absorption lines of Carbon Monoxide. In addition, it can be appreciated that the transmission peaks 904 are very narrow. Accordingly, the filter 408 in accordance with an embodiment of the present invention using a multiple cavity correlation stack 804 can provide a high resolution filter response as well as a high signal-to-noise ratio. As can be appreciated by one of skill in the art, the wavelengths at which the transmission peaks (passbands) 904 are centered may be selected to correlate to any atmospheric gas.

The following examples are provided for purposes of illustration only and are not intended to limit the scope of the invention.

EXAMPLE 1

This example correlation filter 408 utilizes a single etalon. In particular, the design utilizes a solid silicon etalon 1004 that is 386.55 um thick with a total of 39 layers of Ge and SiO, with 9 layers 1008 deposited on the front side and 30 layers 1012 deposited on the back side of the etalon 1004 as shown conceptually in FIG. 10. Silicon provides a high refractive index, good thermal properties and good optical quality pieces are widely available. Preliminary prototype etalon fabrication studies show that silicon etalons can be made to precise thickness (+/−0.3 um of target thickness). As can be appreciated by one of skill in the art, minor corrections of thickness errors can be made through temperature tuning to effect a change in the optical path length. In addition, surface roughness of 2.5 nm and local parallelism of <0.5 micro radians can be routinely achieved. Measurements show etalon flatness to be ~3λ, but this may have been influenced in the prototype by how the piece was mounted during test. The unconventional multilayer coating provides sufficient phase dispersion with wavenumber to improve the match between transmission peaks and CO line centers when compared to a traditional etalon design with metallic or quarter wave reflector layers. To improve on the mechanical and thermal integrity of the filter, the filter can be optically contacted to a thick monolithic piece of silicon 1016. The substrate 1016 can be wedged and have an anti-reflective coating 1020 applied on the exit face to minimize its interaction with the filter, reducing or eliminating undesirable channel spectra. The 30 layer coating between the Si etalon and substrate is designed to provide good matching to the substrate refractive index, in addition to wavenumber-dependent phase dispersion to tune the transmission peak locations. Preliminary design analysis shows that 12 transmission peaks match the positions of CO line centers to within +/−0.04 cm$^{-1}$ with a transmission value >95% from the etalon into the silicon substrate. The layer materials Ge (n=4.1) and SiO (n=2.89) are compatible with deposition on silicon and have the added advantage that their individual coating-induced mechanical stresses tend to compensate each other over many layers.

The phase-compensation coating design allows a convenient means to improve peak transmission of an optically-contacted etalon compared to a free-standing etalon through optimization of the matching layer (between the coating stack and the Si substrate) and at the same time optimize for narrow passbands. It is possible to reduce the number of layers by matching fewer CO lines if total layer thickness becomes a fabrication issue. Preliminary analysis shows this design to be reasonably robust to layer thickness errors on the order of 1%. The effect of errors is to systematically shift the peaks in unison in wavelength. Positioning of the transmission peak characteristic curve to a more optimal position at shorter wavelengths along the CO line wing can be easily accomplished by tilt-tuning the etalon.

Figure 10:
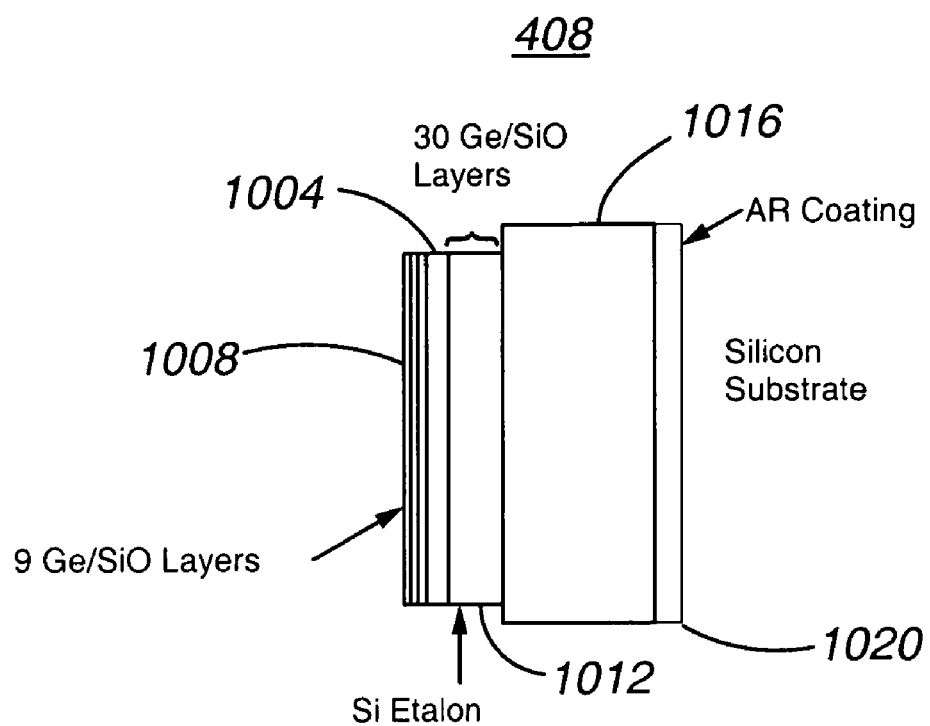
FIG. 10 depicts a correlation filter in accordance with another embodiment of the present invention.
Figure 11:
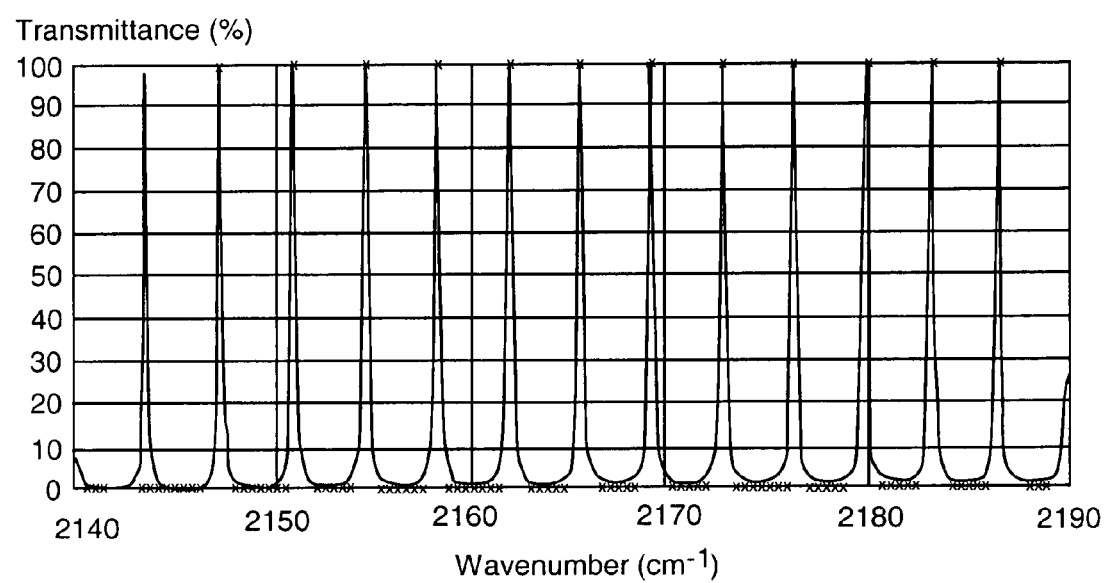
FIG. 11 illustrates transmission peaks of the filter of FIG. 10 over a first range of wave numbers ($cm^{-1}$)
Figure 12:
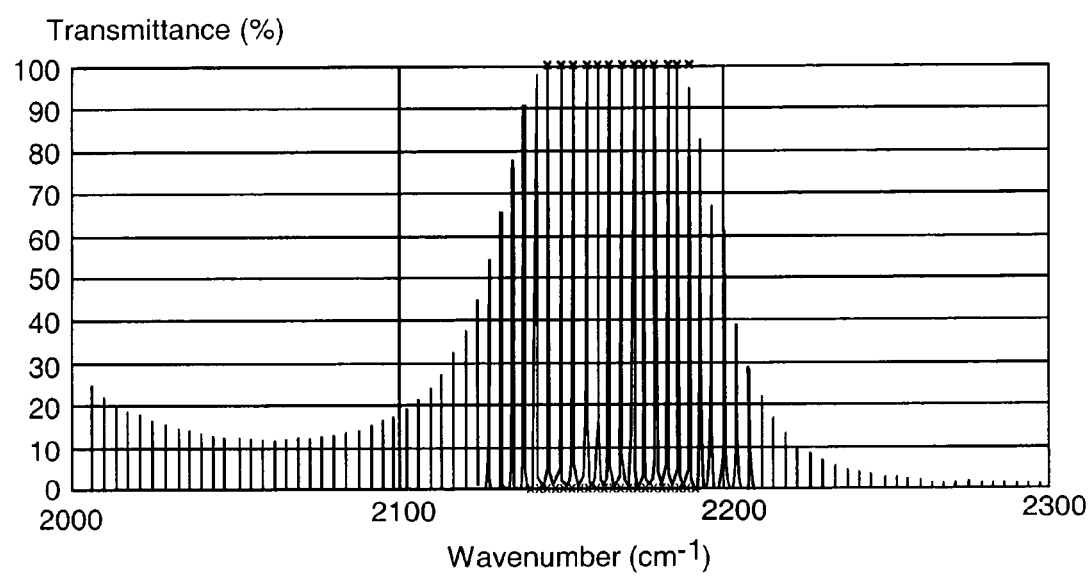
FIG. 12 illustrates transmission peaks of the filter of FIG. 10 over a second range of wave numbers ($cm^{-1}$)

Predicted spectral transmission of the silicon etalon correlation filter 408 of FIG. 10 is shown in FIG. 11. The crosses at 100% transmission are the design targets for matching the line centers of the first 12 lines in the R-branch of CO. Targets at zero in the inter-order region are used to optimize filter rejection between spectral lines. FIG. 12 shows the same transmission function as FIG. 11, but over a wider range of wavenumbers. Orders outside of the R-branch lines of interest roll-off to a level of ~20%. A steep-edged 35 cm$^{-1}$ passband blocking filter may be added to reduce these spurious orders to an acceptable level.

Table 1 sets forth the various layers of this first example correlation filter.

TABLE 1

| Design: | | EXAMPLE 1 | |
| Reference Wavelength (nm): | | 4657.49 | |
| Incident Angle (deg): | | 0 | |

| Layer Medium | Material Air | Refractive Index 1 | Thickness [nm] |
| --- | --- | --- | --- |
| 1 | Ge | 4.074 | 1133.35 |
| 2 | SiO | 2.2888 | 508.73 |
| 3 | Ge | 4.074 | 264.19 |
| 4 | SiO | 2.2888 | 473.01 |
| 5 | Ge | 4.074 | 332.41 |
| 6 | SiO | 2.2888 | 567.99 |
| 7 | Ge | 4.074 | 350.27 |
| 8 | SiO | 2.2888 | 525.96 |
| 9 | Ge | 4.074 | 250.31 |
| 10 | Si | 3.42736 | 386554.6 |
| 11 | Ge | 4.074 | 331.57 |
| 12 | SiO | 2.2888 | 168.68 |
| 13 | Ge | 4.074 | 373.74 |
| 14 | SiO | 2.2888 | 593.49 |
| 15 | Ge | 4.074 | 867.8 |
| 16 | SiO | 2.2888 | 727.3 |
| 17 | Ge | 4.074 | 1039.14 |
| 18 | SiO | 2.2888 | 478.8 |
| 19 | Ge | 4.074 | 829.93 |
| 20 | SiO | 2.2888 | 1439.86 |
| 21 | Ge | 4.074 | 276.32 |
| 22 | SiO | 2.2888 | 487.47 |
| 23 | Ge | 4.074 | 248.15 |
| 24 | SiO | 2.2888 | 470.27 |
| 25 | Ge | 4.074 | 284.78 |
| 26 | SiO | 2.2888 | 329.39 |
| 27 | Ge | 4.074 | 279.06 |
| 28 | SiO | 2.2888 | 332.4 |
| 29 | Ge | 4.074 | 272.23 |
| 30 | SiO | 2.2888 | 353.92 |
| 31 | Ge | 4.074 | 194.99 |
| 32 | SiO | 2.2888 | 382.67 |
| 33 | Ge | 4.074 | 207.82 |
| 34 | SiO | 2.2888 | 337.6 |
| 35 | Ge | 4.074 | 264.24 |
| 36 | SiO | 2.2888 | 611.9 |
| 37 | Ge | 4.074 | 255.1 |
| 38 | SiO | 2.2888 | 38.68 |
| 39 | Ge | 4.074 | 100.59 |
| 40 | SiO | 2.2888 | 537.83 |
| Substrate | Si | 3.42736 | |

EXAMPLE 2

Figure 13:
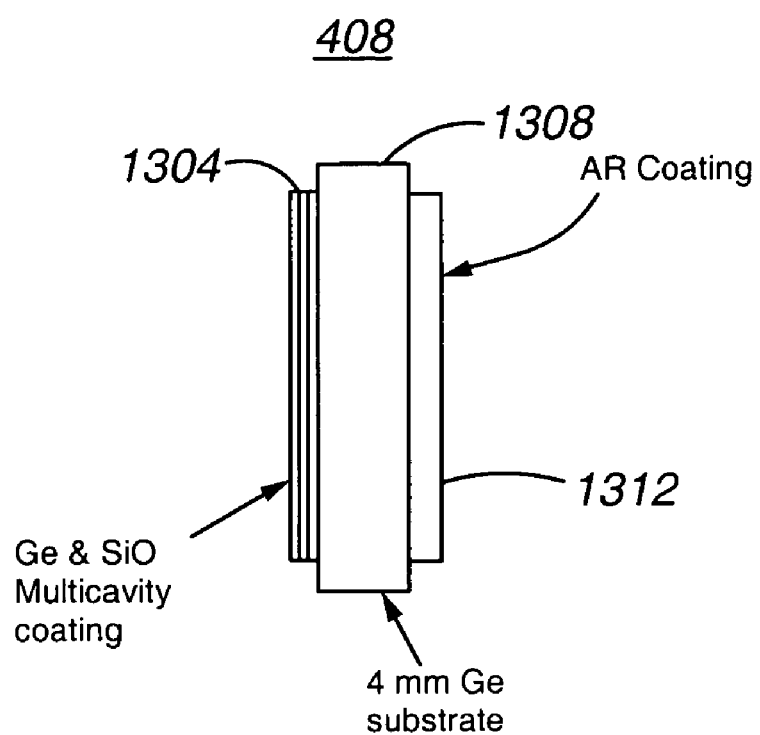
FIG. 13 depicts a correlation filter in accordance with another embodiment of the present invention.

This example correlation filter 408, depicted in FIG. 13, uses a series of asymmetric Ge/SiO spacer and coupling layers 1304 having non-quarterwave thickness. This represents a departure from the periodic design approach of the prior art for producing interference filters with multiple peaks. The change in spectral line spacing of linear molecules CO and $CO_2$ is cubic in nature requiring a higher degree of design freedom than allowed for by a periodic structure. Allowing the design to be asymmetric with non-quarterwave layer thickness provides the needed additional degrees of freedom. The filter stack 1304 can be deposited onto a thick Ge substrate 1308 to make the filter shock and vibration tolerant. Desirable features for the filter include positions of peak transmission that coincide with the CO line centers' peak positions, and film transmission between peaks. The design goal was to match 4 to 5 orders within +/−0.05 cm$^{-1}$. Reducing the number of target lines matched by the filter from a number greater than 5 improved the resultant layer thickness profiles (from the view of fabrication) and inter-band rejection. In addition relaxing the requirement to match adjacent CO lines also enabled improved the resultant filter spectral characteristic.

This exemplary filter design comprises a 62-layer Ge/SiO stack 1304 on a 4 mm Ge substrate 1308. In addition, an antireflective coating 1312 may be included. Five CO lines are matched with this design to within approximately +/−0.02 cm$^{-1}$ (assuming some small amount of tilt-tuning). Peak transmission is >90% for all passbands. The resulting spectral widths of the transmission passbands are <0.4 cm$^{-1}$, because it is believed that further design optimization may achieve a passband width of 0.1 cm$^{-1}$. One of the very desirable aspects of this exemplary design is the strongly $H_2O$-contaminated CO line near 2162 cm$^{-1}$ is avoided. In addition, out-band rejection beyond the 5-orders of interest eases requirements for a narrow passband blocking filter. Layer tolerances should be within about ~0.11 to 0.2%.

Figure 14:
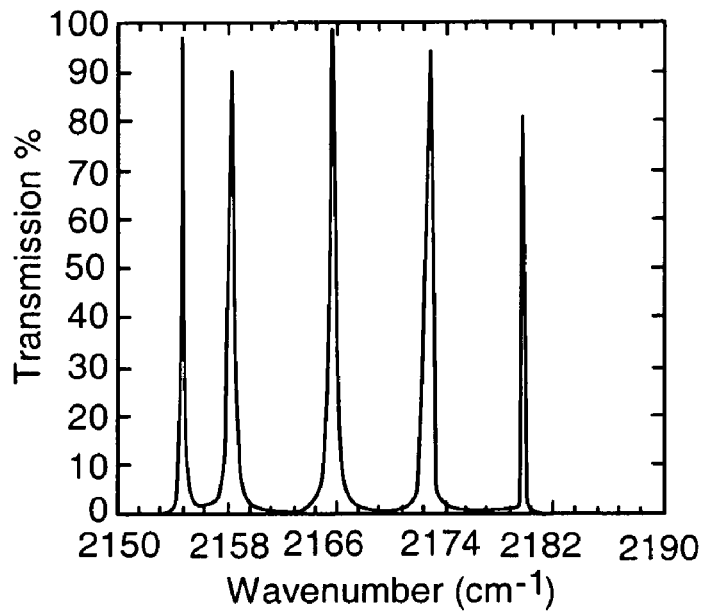
FIG. 14 illustrates transmission peaks of the filter of FIG. 13.
Figure 15:
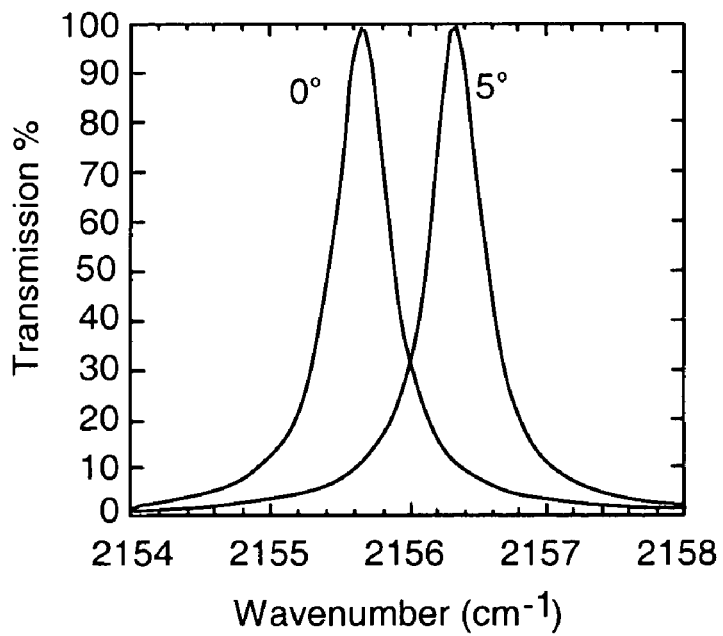
FIG. 15 illustrates the shift in transmission wavelength with angle for the filter of FIG. 13.
Figure 16:
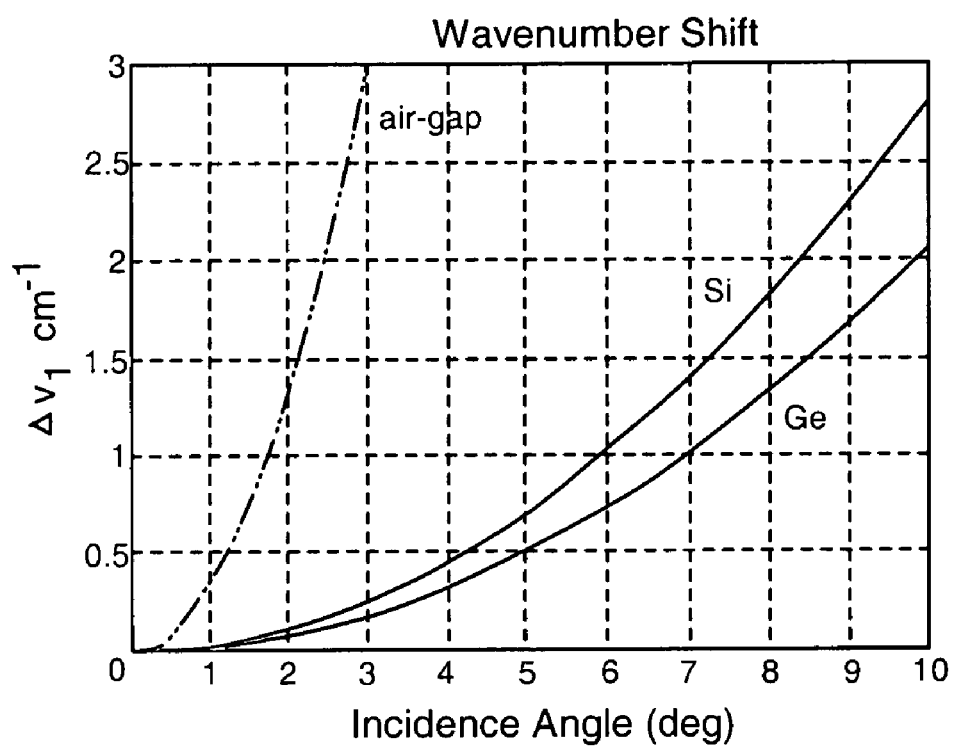
FIG. 16 illustrates the wavelength shift as a function of effective index of refraction for the filter of FIG. 13.
Figure 17:
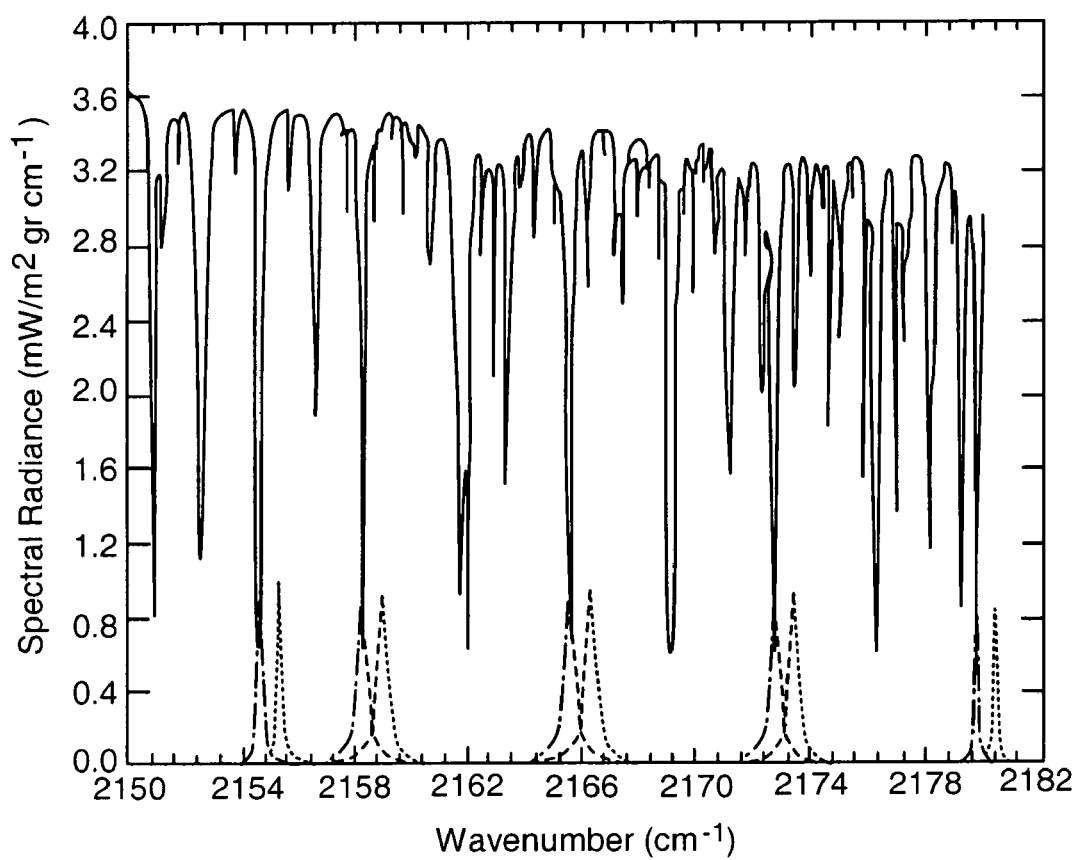
FIG. 17 illustrates the relationship between the filter transmission peaks for the filter of FIG. 13 and absorption lines for CO.

Transmission peaks are centered at 2179.77 cm$^{-1}$, 2172.76 cm$^{-1}$, 2165.63 cm$^{-1}$, 2158.28 cm$^{-1}$, and 2154.60 cm$^{-1}$ corresponding to the 2179.7719 cm$^{-1}$, 2172.7588 cm$^1$, 2165.6010 cm$^{-1}$, 2158.2997 cm$^{-1}$, and 2154.5956 cm$^{-1}$ spectral lines of absorption of CO (see FIG. 14). The shift in peak transmission at 5-degrees is 0.7 cm$^{-1}$ (See FIG. 15). Some of the candidate filter designs showed moderate polarization sensitivity at a 5-degree incidence angle. Filter transmission at several incidence angles was calculated and the effective index of refraction of the filter was derived from this dependence: $n^* \approx \sqrt{n_H n_L} = 3.34$. The results are plotted in FIG. 16 using the equation for small angles: $\partial\lambda = \lambda\theta^2/(2n^2)$. The relationship between the transmission peaks at 0° and at 5° angle of incidence for the correlation filter 408 of this second example and the spectral lines of absorption of CO is illustrated in FIG. 17.

Table 2 sets forth the various layers of the second example correlation filter.

TABLE 2

| Design: | targc_do4_02_b_o6 |
|---|---|
| Reference Wavelength (nm): | 4615 |
| Incident Angle (deg): | 0 |

| Layer | Medium Material Air | Refractive Index 1 | Thickness [nm] |
|---|---|---|---|
| 1 | SiO | 2.2888 | 8139.32 |
| 2 | Ge | 4.074 | 397.53 |
| 3 | SiO | 2.2888 | 96.67 |
| 4 | Ge | 4.074 | 416.7 |
| 5 | SiO | 2.2888 | 367.72 |
| 6 | Ge | 4.074 | 4187.11 |
| 7 | SiO | 2.2888 | 6526.32 |
| 8 | Ge | 4.074 | 2996.41 |
| 9 | SiO | 2.2888 | 2423.11 |
| 10 | Ge | 4.074 | 282.29 |
| 11 | SiO | 2.2888 | 515.18 |
| 12 | Ge | 4.074 | 281.65 |
| 13 | SiO | 2.2888 | 504.01 |
| 14 | Ge | 4.074 | 845.39 |
| 15 | SiO | 2.2888 | 503.97 |
| 16 | Ge | 4.074 | 1699.13 |
| 17 | SiO | 2.2888 | 504.17 |
| 18 | Ge | 4.074 | 845.43 |
| 19 | SiO | 2.2888 | 506.72 |
| 20 | Ge | 4.074 | 261.6 |
| 21 | SiO | 2.2888 | 545.7 |
| 22 | Ge | 4.074 | 135.87 |
| 23 | SiO | 2.2888 | 2.36 |
| 24 | Ge | 4.074 | 177.25 |
| 25 | SiO | 2.2888 | 528.07 |
| 26 | Ge | 4.074 | 285.62 |
| 27 | SiO | 2.2888 | 504.64 |
| 28 | Ge | 4.074 | 1700.57 |
| 29 | SiO | 2.2888 | 504.72 |
| 30 | Ge | 4.074 | 283.85 |
| 31 | SiO | 2.2888 | 508.34 |
| 32 | Ge | 4.074 | 284.16 |
| 33 | SiO | 2.2888 | 511.5 |
| 34 | Ge | 4.074 | 273 |
| 35 | SiO | 2.2888 | 480.09 |
| 36 | Ge | 4.074 | 40.23 |
| 37 | SiO | 2.2888 | 680 |
| 38 | Ge | 4.074 | 149.67 |
| 39 | SiO | 2.2888 | 440 |
| 40 | Ge | 4.074 | 809.9 |
| 41 | SiO | 2.2888 | 459.12 |
| 42 | Ge | 4.074 | 266 |
| 43 | SiO | 2.2888 | 453.63 |
| 44 | Ge | 4.074 | 149.45 |
| 45 | SiO | 2.2888 | 1.8 |
| 46 | Ge | 4.074 | 130.81 |
| 47 | SiO | 2.2888 | 504.64 |
| 48 | Ge | 4.074 | 283.62 |
| 49 | SiO | 2.2888 | 504.68 |
| 50 | Ge | 4.074 | 1699.07 |
| 51 | SiO | 2.2888 | 503.78 |
| 52 | Ge | 4.074 | 282.89 |
| 53 | SiO | 2.2888 | 504.41 |
| 54 | Ge | 4.074 | 282.43 |
| 55 | SiO | 2.2888 | 505.77 |
| 56 | Ge | 4.074 | 282.09 |
| 57 | SiO | 2.2888 | 503.73 |
| 58 | Ge | 4.074 | 283.76 |
| 59 | SiO | 2.2888 | 503.68 |
| 60 | Ge | 4.074 | 1699.02 |
| 61 | SiO | 2.2888 | 504.29 |
| 62 | Ge | 4.074 | 283.22 |
| 63 | SiO | 2.2888 | 503.18 |
| 64 | Ge | 4.074 | 283.49 |
| 65 | SiO | 2.2888 | 508.83 |
| 66 | Ge | 4.074 | 287.29 |
| 67 | SiO | 2.2888 | 3552.15 |
| 68 | Ge | 4.074 | 1470.11 |
| 69 | SiO | 2.2888 | 5495 |
| 70 | Ge | 4.074 | 1439.56 |
| 71 | SiO | 2.2888 | 779.63 |
| 72 | Ge | 4.074 | 285.7 |
| 73 | SiO | 2.2888 | 671.76 |
| 74 | Ge | 4.074 | 105.46 |
| 75 | SiO | 2.2888 | 1.65 |
| 76 | Ge | 4.074 | 38.97 |
| 77 | SiO | 2.2888 | 103.05 |
| 78 | Ge | 4.074 | 414.23 |
| 79 | SiO | 2.2888 | 56.91 |
| 80 | Ge | 4.074 | 378.99 |
| 81 | SiO | 2.2888 | 1098.86 |
| 82 | Ge | 4.074 | 172.09 |
| 83 | SiO | 2.2888 | 130.64 |
| 84 | Ge | 4.074 | 168.58 |
| 85 | SiO | 2.2888 | 162.94 |
| 86 | Ge | 4.074 | 186.64 |
| 87 | SiO | 2.2888 | 260.9 |
| 88 | Ge | 4.074 | 174.83 |
| 89 | SiO | 2.2888 | 13.45 |
| 90 | Ge | 4.074 | 90.23 |
| 91 | SiO | 2.2888 | 2.78 |
| 92 | Ge | 4.074 | 11.9 |
| 93 | SiO | 2.2888 | 0.08 |
| 94 | Ge | 4.074 | 83.29 |
| 95 | SiO | 2.2888 | 126.04 |
| 96 | Ge | 4.074 | 82.84 |

TABLE 2-continued

| 97 | SiO | 2.2888 | 52.68 |
|---|---|---|---|
| Substrate | Ge | 4.074 | |

From the description provided herein, it can be appreciated that the present invention provides a system for remotely sensing atmospheric trace gas having an increased field of view. In particular, the field angle of light received at the sensor may be compressed in at least a first plane. For example, field angle compression may be performed within a cross-track plane 136, to provide a wide field of view in the cross track direction 128. Such field angle compression may be accomplished by providing an anamorphic telescope optical assembly 404 that provides a magnification power of less than 1.0 in the cross track plane 136, but not in an along-track plane 140. According to an alternative embodiment, field angle compression may be performed in both the cross track 136 and along-track 140 planes, to provide a wide field of view in both the cross-track 128 and along-track 124 directions by providing a telescope optical assembly 404 that has a magnification of less than 1.0 symmetrically about the axis 132 of the sensor system 104.

Furthermore, the present invention provides a system for sensing atmospheric trace gas that is capable of providing information regarding the altitude distribution of such trace gas, in addition to providing an increased field of view. In particular, in an embodiment in which field angle correction is performed in the cross-track plane 136 only, information regarding the altitude distribution of atmospheric gas can be obtained by measuring the absorption of light associated with a ground pixel at different angles to the sensor system 104, to achieve spectral scanning. In particular, because a change in angle in the along-track plane 140 of such an embodiment causes a shift in the transmitted wavelength or wavelengths, measurements with respect to the same ground pixel may be made from different points along the line wing of the gas being measured as the platform 108 moves relative to the Earth 116.

An embodiment in which field angle compression is performed in both the along-track 124 and cross-track 128 directions is particularly useful in connection with a staring array sensor. For example, an embodiment providing symmetrical magnification of less than 1.0 is useful for providing increased signal integration time and/or in connection with a geo-stationary platform 108.

In addition to providing an increased field of view, the present invention provides greater signal integration time, whether the sensor system 104 is implemented as a push broom imager (for example, as part of a low earth orbit satellite or aircraft platforms 108) or as a fixed, staring array sensor (for example as part of a geo-stationary platform 108). The increased integration time provided by embodiments of the present invention allows the aperture of the sensor to be reduced for a given signal to noise ratio, or allows for an increase in the number of spectral samples that can be obtained.

In addition, it will be appreciated that the present invention removes the need to provide a precision scan mechanism. In particular, the present invention provides a wide coverage area or field of view 120 without requiring mechanical scanning.

Although examples of filters 408 comprising correlation filters having non-periodically spaced transmission peaks have been discussed herein, it should be appreciated that a field angle correcting or condensing sensor system 104 in accordance with the present the present invention is not limited to use with such filters. In particular, a field angle correcting or condensing sensor system 104 in accordance with the present invention may operate in connection with a conventional single transmission peak or band, or multiple transmission peak or band, filter 408. Furthermore, it should be appreciated that a filter 408 used in connection with a sensor system 104 in accordance with the present invention may comprise a single cavity interference type filter, such as a Fabry-Perot interferometer or etalon. In addition, a solid or gas-filled etalon may be used with such a filter 408. In accordance with additional embodiments of the present invention, the filter 408 may comprise multiple optical cavities. For example, a filter 408 may be formed conventionally using stacks of thin films.

Although examples set forth above discuss embodiments in which field angle compression is performed in a cross-track 136 plane, this is not required. For example, field angle compression could be performed in the along-track plane 140, but not in the cross-track plane 136, in connection with a platform comprising an aircraft flying a non-linear pattern.

The foregoing discussion of the invention has been presented for purposes of illustration and description. Further, the description is not intended to limit the invention to the form disclosed herein. Consequently, variations and modifications commensurate with the above teachings, within the skill and knowledge of the relevant art, are within the scope of the present invention. The embodiments described hereinabove are further intended to explain the best mode presently known of practicing the invention and to enable others skilled in the art to utilize the invention in such or in other embodiments and with various modifications required by their particular application or use of the invention. It is intended that the appended claims be construed to include the alternative embodiments to the extent permitted by the prior art.

What is claimed is:

1. A field condensing sensor device, comprising:
   a telescope optical system having an input encompassing a first field of view and an output that is magnified by less than one in at least a first plane;
   a filter positioned to receive light output by said telescope, optical system, wherein said filter features a number of passbands, wherein said light output by said telescope optical system within said first plane is incident on said filter within a first maximum angle, wherein said light is incident on said filter within a second maximum angle, and wherein said first maximum angle is less than said second maximum angle; and
   a detector positioned to receive light passed by said filter.

2. The device of claim 1, wherein said telescope optical system comprises an anamorphic telescope, wherein light received at an angle to an axis of said telescope with respect to said first plane is magnified by an amount of less than one, and wherein light received at an angle to an axis of said telescope with respect to a second plane is not magnified.

3. The device of claim 2, wherein said first plane is substantially perpendicular to said second plane.

4. The device of claim 1, wherein said magnification in said at least a first plane is no more than 0.25.

5. The device of claim 1, wherein said magnification in said at least a first plane is no more than 0.1.

6. The device of claim 1, wherein said telescope optical system provides a first magnification with respect to any ray within said first field of view.

7. The device of claim 1, wherein said filter comprises at least a first optical cavity.

8. The device of claim 7, wherein said at least a first optical cavity comprises a material having a high index of refraction.

9. The device of claim 8, wherein said at least a first optical cavity comprises Germanium.

10. The device of claim 7, wherein said at least a first optical cavity is provided as part of an etalon.

11. The device of claim 1, wherein said filter comprises a plurality of optical cavities.

12. The device of claim 1, further comprising a cold stop located between said telescope optical system and said detector.

13. The device of claim 1, wherein said detector comprises a two-dimensional array.

14. The device of claim 1, wherein said filter includes a compensation stack including a plurality of layers, wherein an optical thickness of at least some of said layers of said compensation stack does not equal an integer multiple of one quarter of a wavelength of light having a first wavelength corresponding to a first pass band of said filter device having a first center wavelength, wherein such filter device further comprises a second pass band having a second center wavelength and a third pass band having a third center wavelength, wherein said first center wavelength is separated from said second center wavelength by a first amount, and wherein said second center wavelength is separated from said third center wavelength by a second amount that is not equal to said first amount.

15. A field condensing sensor device, comprising:
a telescope optical system having an input encompassing a first field of view and an output that is magnified by less than one in at least a first plane;
a filter positioned to receive light output by said telescope optical system; and
a detector positioned to receive light passed by said filter, wherein said first field of view is about four degrees, wherein light collected from within said first field of view has a maximum angle of incidence with respect to said filter of no more than one degree in said at least a first plane.

16. A field condensing sensor device, comprising:
a telescope optical system having an input encompassing a first field of view and an output that is magnified by less than one in at least a first plane;
a filter positioned to receive light output by said telescope optical system; and
a detector positioned to receive light passed by said filter, wherein said first field of view is about ten degrees, and wherein light collected from within said field of view has a maximum angle of incidence with respect to said filter of no more than one degree in said at least a first plane.

17. A field condensing sensor device comprising:
a telescopic optical system having an input encompassing a first field of view and an output that is magnified by less than one in at least a first plane;
a detector positioned to receive light passed by said filter, wherein said filter comprises at high index of refraction, wherein a maximum angle of incidence of light collected from within said first field of view that is incident on said filter is no more than one degree in said at least a first plane, and wherein a maximum angle of said light collected from within said first field of view within said optical cavity is less than 0.2 degree.

18. A field condensing sensor device, comprising:
a telescope optical system having an input en compassing a first field of view and an output that is magnified by less than one in at least a first plane;
a filter positioned to receive light output by said telescope optical system;
a detector positioned to receive light passed by said filter, wherein said filter comprises a plurality of optical cavities, and wherein said filter comprises at least a first thin layer reflector stack.

19. A method for remotely sensing atmospheric trace gas, comprising:
collecting light from within a first field of view;
magnifying said collected light in at least a first plane by a magnification factor that is less than one; and
filtering said light magnified in said at least a first plane in a filter having an optical cavity, wherein said filtering comprises substantially blocking light at wavelength not corresponding to a selected number of spectral lines of absorption of an atmospheric trace gas.

20. The method of claim 19, further comprising:
measuring an intensity of said filtered light.

21. The method of claim 19, further comprising:
magnifying said collected light in a second plane by a magnification factor that is less than one.

22. The method of claim 21, wherein said magnification factor in said first plane is equal to said magnification factor in said second plane.

23. The method of claim 19, further comprising:
passing at least one of said collected light and said light magnified in at least a first plane through a cold stop.

24. The method of claim 19, wherein said filter comprises a Fabry-Perot interferometer.

25. A method for remotely sensing atmospheric trace gas, comprising:
collecting light from within a first field of view;
magnifying said collected light in at least a first plane by a magnification factor that is less than one; and
filtering said light magnified in said at least a first plane in a filter having an optical cavity wherein filtering said light comprises passing wavelengths of said magnified light corresponding to spectral lines of absorption of an atmospheric gas.

26. The method of claim 25, further comprising:
measuring an intensity of said filtered light; and
correlating said measured intensity to a concentration of said atmospheric gas within at least a portion of said first field of view.

27. The method of claim 25, wherein filtering said light further comprises attenuating wavelength of said magnified light outside of a first range of wavelengths.

28. A system for remotely sensing atmospheric trace gas, comprising:
means for condensing a field angle of light collected from within a first field of view within at least a first plane, wherein an output of said means for condensing comprises light having a condensed field angle within said at least a first plane; and
means for filtering said light having a condensed field angle, wherein said field angle is measured with respect to a surface of said means for filtering.

29. The system of claim 28, wherein said means for condensing further functions to condense a field angle of light collected from within said first field of view within a second plane that is perpendicular to said first plane.

30. The system of claim 28, wherein said means for filtering comprises optical cavity means including an optical cavity having a high index of refraction.

31. The system of claim 28, further comprising:
means for measuring an intensity of said filtered light.

32. The system of claim 28, further comprising:
means for blocking unwanted background radiation.

33. A system for remotely sensing atmospheric trace gas, comprising:

means for condensing a field angle of light collected from within a first field of view within at least a first plane; and means for filtering said light having, a condensed field angle, wherein said first field of view is greater than about 4 degrees.

* * * * *

UNITED STATES PATENT AND TRADEMARK OFFICE
CERTIFICATE OF CORRECTION

PATENT NO. : 7,030,991 B1  
APPLICATION NO. : 10/633468  
DATED : April 18, 2006  
INVENTOR(S) : Kampe et al.

It is certified that error appears in the above-identified patent and that said Letters Patent is hereby corrected as shown below:

Column 19, Claim 17, between the text ending on line 59 and the text beginning on line 60, add the following: --a filter positioned to receive light output by said telescope optical system; and--

Signed and Sealed this

First Day of August, 2006

JON W. DUDAS  
*Director of the United States Patent and Trademark Office*